(12) United States Patent
Zhou et al.

(10) Patent No.: US 11,135,452 B2
(45) Date of Patent: Oct. 5, 2021

(54) RADIATION SYSTEMS FOR RADIATION TREATMENT AND IMAGING

(71) Applicant: SHANGHAI UNITED IMAGING HEALTHCARE CO., LTD., Shanghai (CN)

(72) Inventors: Jingjie Zhou, Shanghai (CN); Li Wang, Shanghai (CN); Yifeng Jiang, Shanghai (CN); Cheng Ni, Shanghai (CN); Johannes Stahl, Concord, CA (US); Jonathan Maltz, Concord, CA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 211 days.

(21) Appl. No.: 16/286,494

(22) Filed: Feb. 26, 2019

(65) Prior Publication Data
US 2019/0336795 A1    Nov. 7, 2019

Related U.S. Application Data

(63) Continuation of application No. PCT/CN2018/085266, filed on May 2, 2018.

(51) Int. Cl.
*A61N 5/10* (2006.01)
*A61B 6/00* (2006.01)

(52) U.S. Cl.
CPC .......... *A61N 5/1081* (2013.01); *A61B 6/4085* (2013.01); *A61N 5/1045* (2013.01);
(Continued)

(58) Field of Classification Search
None
See application file for complete search history.

(56) References Cited

U.S. PATENT DOCUMENTS

| 4,426,715 A * | 1/1984 | Baer ................... A61B 6/4085 378/4 |
| 5,548,627 A | 8/1996 | Swerdloff et al. |

(Continued)

FOREIGN PATENT DOCUMENTS

| CN | 108514694 A | 9/2018 |
| DE | 102011081422 B4 | 7/2013 |

(Continued)

OTHER PUBLICATIONS

International Search Report in PCT/CN2018/085266 dated Jan. 30, 2019, 5 pages.

(Continued)

*Primary Examiner* — Hoon K Song
(74) *Attorney, Agent, or Firm* — Metis IP LLC

(57) ABSTRACT

A radiation system is provided. The radiation system may include a bore accommodating an object, a rotary ring, a first radiation source and a second radiation source mounted on the rotary ring and a processor. The first radiation source may be configured to emit a first cone beam toward a first region of the object. The second radiation source may be configured to emit a second beam toward a second region of the object, the second region including at least a part of the first region. The processor may be configured to obtain a treatment plan of the object, the treatment plan including parameters associated with radiation segments. The processor may be further configured to control an emission of the first cone beam and/or the second beam based on the parameters associated with the radiation segments to perform a treatment and a 3-D imaging simultaneously.

23 Claims, 16 Drawing Sheets

(52) U.S. Cl.
CPC ......... *A61N 5/1049* (2013.01); *A61N 5/1075* (2013.01); *A61N 5/1071* (2013.01); *A61N 2005/1061* (2013.01)

(56) References Cited

U.S. PATENT DOCUMENTS

| | | |
|---|---|---|
| 5,751,781 A | 5/1998 | Brown et al. |
| 6,914,959 B2 | 7/2005 | Bailey et al. |
| 7,245,698 B2 | 7/2007 | Pang et al. |
| 7,519,151 B1 | 4/2009 | Shukla et al. |
| 8,804,901 B2 | 8/2014 | Maurer, Jr. et al. |
| 9,687,200 B2 | 6/2017 | Maurer, Jr. |
| 9,724,049 B2 | 8/2017 | Umekawa et al. |
| 10,315,049 B2 | 6/2019 | Gauthier et al. |
| 2005/0201509 A1 | 9/2005 | Mostafavi et al. |
| 2006/0064008 A1 | 3/2006 | Moore |
| 2007/0016014 A1 | 1/2007 | Hara et al. |
| 2009/0251709 A1 | 10/2009 | Kindlein |
| 2010/0183118 A1 | 7/2010 | Star-Lack et al. |
| 2010/0202588 A1 | 8/2010 | Shibuya et al. |
| 2010/0208274 A1 | 8/2010 | Kindlein et al. |
| 2011/0006224 A1 | 1/2011 | Maltz et al. |
| 2011/0080990 A1 | 4/2011 | Filiberti et al. |
| 2011/0085640 A1 | 4/2011 | Fadler |
| 2011/0313231 A1* | 12/2011 | Guertin ............... A61N 5/1069 600/1 |
| 2012/0230464 A1* | 9/2012 | Ling ................... A61B 6/4085 378/9 |
| 2013/0158382 A1 | 6/2013 | Chao |
| 2016/0271423 A1 | 9/2016 | Takahashi |
| 2018/0056090 A1 | 3/2018 | Jordan et al. |

FOREIGN PATENT DOCUMENTS

| | | |
|---|---|---|
| DE | 102011075341 B4 | 5/2014 |
| EP | 2630989 A1 | 8/2013 |
| EP | 2197352 B1 | 7/2016 |
| EP | 2633293 B1 | 5/2019 |
| EP | 3569289 B1 | 12/2020 |
| WO | 1999035966 A1 | 7/1999 |
| WO | 2002022210 A1 | 3/2002 |
| WO | 2004033027 A2 | 4/2004 |
| WO | 2016000777 A1 | 1/2016 |

OTHER PUBLICATIONS

Written Opinion in PCT/CN2018/085266 dated Jan. 30, 2019, 3 pages.

* cited by examiner

1500

```
Obtain an adjusted treatment plan, the adjusted treatment plan
including parameters associated with one or more radiation
segments, which includes a desired (or an adjusted) segment
shape, a desired (or an adjusted) segment intensity, a desired (or
an adjusted) segment angle range, and/or a desired (or an
adjusted) relative position of the object relative to the rotary ring
```
↘ 1510

↓

```
Move the MLC according to the desired (or an adjusted) segment
shape when a desired (or an adjusted) segment angle range is
reached during the rotation of the rotary ring
```
↘ 1520

↓

```
Control the emission of the first beam and/or the second beam
from the first radiation source and/or the second radiation source
based on the desired (or an adjusted) segment intensity
```
↘ 1530

↓

```
Move the scanning bed based on the desired (or an adjusted)
relative position of the object with respect to the rotary ring
```
↘ 1540

FIG. 15

RADIATION SYSTEMS FOR RADIATION TREATMENT AND IMAGING

CROSS-REFERENCE TO RELATED APPLICATION

This application is a Continuation of International Application No. PCT/CN2018/085266, filed on May 2, 2018, the contents of which is incorporated herein by reference.

TECHNICAL FIELD

The present disclosure generally relates to radiation systems, and more specifically relates to radiation delivery devices including a treatment radiation source and an imaging radiation source mounted on a rotary ring.

BACKGROUND

Radiotherapy has been widely employed in cancer treatment in which ionizing radiation is guided towards a tumor region. Considerations of radiotherapy include that the tumor receives sufficient radiation, while the damage to an organ at risk (OAR) is minimized as much as possible during the radiotherapy. The tumor and/or the OAR may be in motion due to a physiological motion (e.g., respiratory motion, cardiac motion, muscle contraction, and relaxation) of the object under the treatment. The tumor region may change with such motion of the object. However, under traditional radiotherapy systems, the area where the radiation impinging upon an object is often fixed, and the change of the tumor region due to the motion of the object may cause more damage to OARs and the radiation efficacy to deteriorate. Thus, it is desirable to design a system capable of detecting the motion of the tumor and adjusting the radiation to the tumor region accordingly.

SUMMARY

According to an aspect of the present disclosure, a radiation system is provided. The radiation system may include: a bore configured to accommodate an object, a rotary ring, a first radiation source mounted on the rotary ring, a second radiation source mounted on the rotary ring and a processor. The first radiation source may be configured to emit a first cone beam toward a first region of the object, with a 2-D collimator positioned between a center of the bore and the first radiation source to form at least one aperture, the aperture modifying a shape of the first cone beam. The second radiation source may be configured to emit a second beam toward a second region of the object, the second region including at least a part of the first region. The processor may be configured to cause the radiation system to obtain a treatment plan of the object, the treatment plan including parameters associated with one or more radiation segments. The processor may be further configured to cause the radiation system to cause the rotary ring to rotate around the object in one direction continuously for at least two full rotations. The processor may be further configured to cause the radiation system to adjust the at least one aperture of the 2-D collimator based on the parameters associated with the one or more radiation segments. The processor may be further configured to cause the radiation system to control an emission of at least one of the first cone beam or the second beam based on the parameters associated with the one or more radiation segments to perform a treatment and a 3-D imaging simultaneously.

In some embodiments, the 2-D collimator may include a multi-leaf collimator (MLC) including a plurality of leaves to form the aperture.

In some embodiments, when the rotary ring rotates, an angular offset between the first radiation source and the second radiation source in a plane of the rotation of the rotary ring remains unchanged.

In some embodiments, the parameters associated with the one or more radiation segments include at least one of a desired segment shape, a desired segment MU value, a desired segment MU rate, a desired segment angle range, or a desired relative position of the object relative to the rotary ring.

In some embodiments, the radiation system further includes a radiation detector configured to detect radiation impinging on the radiation detector. The processor is further configured to cause the radiation system to obtain treatment planning image data of the object associated with the treatment plan. The processor is further configured to cause the radiation system to generate a radiograph or CT image data based on the detected radiation by the radiation detector, the detected radiation being associated with at least one of the first cone beam or the second beam. The processor is further configured to cause the radiation system to compare the generated radiograph or CT image data with the treatment planning image data. The processor is further configured to cause the radiation system to determine whether the treatment plan needs to be adjusted based on a result of the comparison between the generated radiograph or CT image data and the treatment planning image data. The processor is further configured to cause the radiation system to adjust, based on a result of the determination that the treatment plan needs to be adjusted, at least one of the parameters associated with the one or more radiation segments.

In some embodiments, the radiograph or the CT image data is obtained during a part of a rotation of the rotary ring.

In some embodiments, the radiation system may further include a bed configured to support the object, wherein the processor is further configured to cause the radiation system to adjust a position of the bed based on a desired position of the object with respect to the rotary ring.

In some embodiments, the processor is further configured to cause the radiation system to obtain respiration information of the object. The processor is further configured to cause the radiation system to determine a rotation parameter of the rotary ring based on the respiration information of the object. The processor is further configured to cause the radiation system to control a rotation of the rotary ring based, at least in part, on the determined rotation parameter.

In some embodiments, the rotation parameter includes a rotation speed.

In some embodiments, within a period that the rotary ring rotates a full rotation, the first radiation source emits the first cone beam and the second radiation source emits a second beam.

In some embodiments, a period that the rotary ring rotates a full rotation is less than 30 seconds.

In some embodiments, the radiation system may further include a radiation detector configured to detect radiation impinging upon the detector. The processor is further configured to cause the radiation system to cause the rotary ring to rotate a first full rotation and a second full rotation, the second full rotation being after the first full rotation. The processor is further configured to cause the radiation system to adjust, based on radiation detected by the radiation detector in the first full rotation, parameters associated with the radiation segments at which the first radiation source emits a first cone beam in the second full rotation. The processor is further configured to cause the radiation system to control an emission of the first cone beam based on the adjusted parameters associated with the radiation segments.

In some embodiments, the radiation system may further include a radiation detector configured to detect radiation impinging upon the detector. The processor is further configured to cause the radiation system to cause the rotary ring to rotate. The processor is further configured to cause the radiation system to adjust, based on radiation detected by the radiation detector in the present rotation, parameters associated with radiation segments that follow the radiation detection by the radiation detector in the present rotation. The processor is further configured to cause the radiation system to control an emission of the first cone beam at the radiation segments that follow the radiation detection by the radiation detector based on the adjusted parameters associated with the radiation segments that follow the radiation detection by the radiation detector in the present rotation.

In some embodiments, a rotation of the rotary ring is driven via at least one of a slip ring, a gear, a reel, or a rotation shaft.

In some embodiments, the radiation system may further include a movement restriction component configured to limit a movement of the rotary ring.

In some embodiments, a cone angle of the second beam is greater than or equal to a cone angle of the first cone beam.

In some embodiments, the radiation system may further include a CT detector configured to detect radiation emitted by the second radiation source after attenuation by the object.

In some embodiments, the radiation system may further include a flat panel detector configured to detect radiation emitted by the first radiation source after attenuation by the object.

In some embodiments, the radiation system may further include a bed configured to support the object and move in a first direction. The processor is further configured to cause the radiation system to move the first radiation source in the first direction.

In some embodiments, the first radiation source moves at a speed equal to a speed of the bed.

In some embodiments, the radiation system may further include a bed configured to support the object and move in a first direction. The processor is further configured to cause the radiation system to dispose the 2-D collimator of the first radiation source to move in the first direction.

In some embodiments, the 2-D collimator of the first radiation source moves at a speed equal to a moving speed of the bed.

In some embodiments, to perform the 3-D imaging, the processor is configured to cause the system to generate a 3-D image based on a received radiation associated with the first cone beam and the second beam.

In some embodiments, to perform the 3-D imaging, the processor is configured to cause the system to generate a 3-D image based on a received radiation associated with the first cone beam and the second beam emitted in a same full rotation.

In some embodiments, to perform the 3-D imaging, the processor is configured to cause the system to generate a 3-D image based on a received radiation associated with the first cone beam and the second beam emitted in a same fraction of a full rotation.

According to another aspect of the present disclosure, a radiation system is provided. The radiation system may include a bore configured to accommodate an object, a rotary ring, a first radiation source mounted on the rotary ring, a second radiation source mounted on the rotary ring, and a processor. The first radiation source may be configured to emit a first cone beam toward a first region of the object, with a 2-D collimator positioned between a center of the bore and the first radiation source to form at least one aperture, the aperture modifying a shape of the first cone beam. The second radiation source may be configured to emit a second beam toward a second region of the object, the second region including at least a part of the first region. The processor may be configured to cause the radiation system to obtain a treatment plan of the object, the treatment plan including parameters associated with one or more radiation segments. The processor may be further configured to adjust a position of the object relative to the first cone beam based on the parameters associated with the one or more radiation segments. The processor may be further configured to control an emission of at least one of the first cone beam or the second beam based on the parameters associated with the one or more radiation segments to perform a treatment and a 3-D imaging simultaneously.

In some embodiments, images generated by the second radiation source are used to modify the position of the object with respect to the first radiation source such that target tissue in the first region is centered at an isocenter of the radiation system.

In some embodiments, the target tissue in the first region is partitioned into subvolumes, the subvolumes being treated serially during different rotation angles of the rotary ring. The processor is further configured to cause the radiation system to adjust a position of at least one of the subvolumes such that a center of the at least one of the subvolumes substantially overlaps with the isocenter of the radiation system.

In some embodiments, respiration information is used to modify the position of the object with respect to the first radiation source such that target tissue in the first region is substantially centered at an isocenter of the radiation system.

In some embodiments. the target tissue in the first region is partitioned into subvolumes, the subvolumes being treated serially during different rotation angles of the rotary ring. The processor is further configured to cause the radiation system to adjust a position of at least one of the subvolumes such that a center of the at least one of the subvolumes substantially overlaps with the isocenter of the radiation system.

In some embodiments, to perform the 3-D imaging, the processor is configured to cause the system to generate a 3-D image based on a received radiation associated with the first cone beam and the second beam.

In some embodiments, to perform the 3-D imaging, the processor is configured to cause the system to generate a 3-D image based on a received radiation associated with the first cone beam and the second beam emitted in a same full rotation.

In some embodiments, to perform the 3-D imaging, the processor is configured to cause the system to generate a 3-D image based on a received radiation associated with the first cone beam and the second beam emitted in a same fraction of a full rotation.

In some embodiments, electric power may be transferred to the first radiation source and the second radiation source via a slip ring.

In some embodiments, a detector may be paired with the second radiation source, configured to detect radiation associated with the second beam. Control and imaging data may be transferred to and from the paired second radiation source and detector via a slip ring.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 15 is a flowchart illustrating an exemplary process for adjusting one or more components of the radiation system based on the adjusted treatment plan.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "object" and "subject" may be used interchangeably as a reference to a thing that undergoes a treatment and/or an imaging in a radiation system of the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
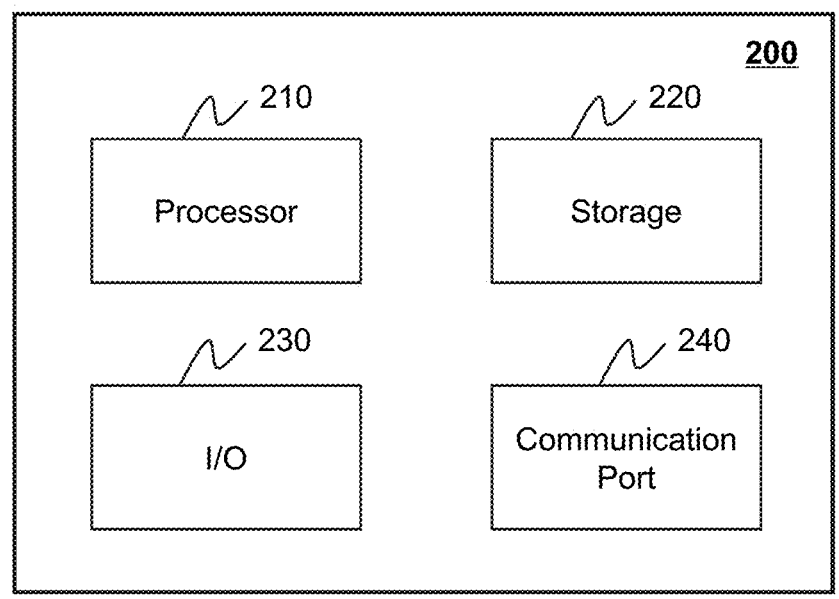
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

An aspect of the present disclosure relates to a radiation delivery device for imaging an object (also referred to as a subject) during radiotherapy. The radiation delivery device disclosed in the present disclosure includes an imaging radiation source and a treatment radiation source both mounted on a rotary ring. The rotary ring may rotate around the object. With the radiation delivery device, the object may be imaged and treated in a rotation of the rotary ring. The treatment in a rotation of the rotary ring may depend on the image data generated according to a preceding rotation. A treatment plan may be used to control the radiation delivery device. The treatment plan may be adjusted based on the image data and the original treatment plan.

Figure 1:
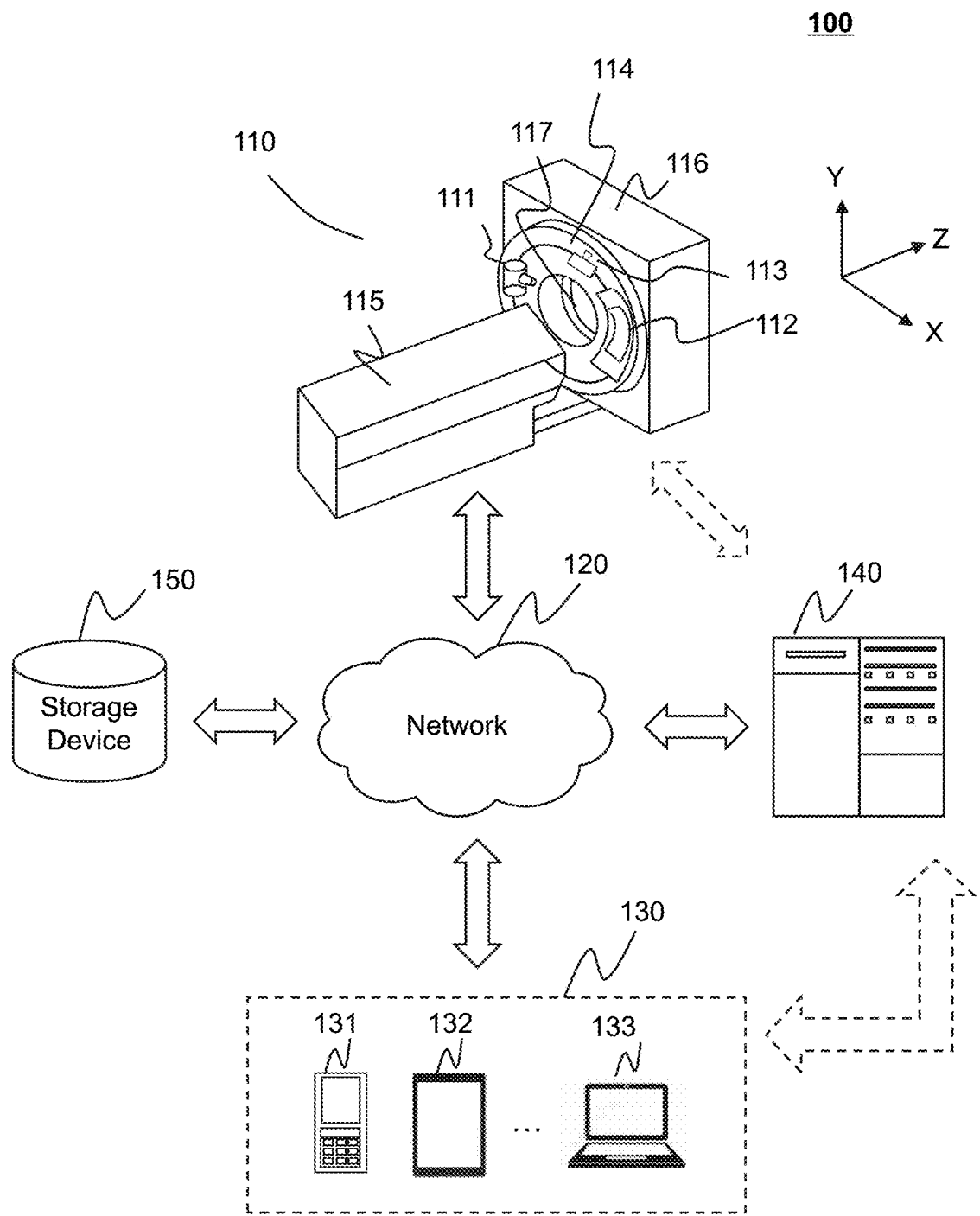
FIG. 1 is a schematic diagram illustrating an exemplary radiation system according to some embodiments of the present disclosure.

FIG. 1 is a schematic diagram illustrating an exemplary radiation system 100 according to some embodiments of the present disclosure. The radiation system 100 may include a radiation delivery device 110, a network 120, one or more terminals 130, a processing device 140, and a storage device 150.

The radiation delivery device 110 may include a first radiation source 113 and a second radiation source 111. The examples of the first radiation source 113 may be found elsewhere in this disclosure (e.g., treatment radiation source 430 illustrated in FIG. 4, treatment radiation source 730 illustrated in FIG. 7). The examples of the second radiation source 111 may be found elsewhere in this disclosure (e.g., treatment radiation source 410 illustrated in FIG. 4, treatment radiation source 710 illustrated in FIG. 7). The first radiation source 113 may emit a first beam (also referred to as a first cone beam) toward a first region of an object (e.g., a patient or a portion thereof). The second radiation source 111 may emit a second beam toward a second region of the object. The second region may overlap with the first region (e.g., the second region may include at least part of the first region). In some embodiments, the first beam and the second beam may each include at least one radiation ray. The radiation ray may include but not limited to X-rays, α-rays, β-rays, γ-rays, heavy ions, etc. Merely by way of example, the first radiation source may be a treatment radiation source, and the first region may correspond to a treatment region (e.g., a tumor). The second radiation source may be an imaging radiation source, and the second region may correspond to an imaging region including at least part of the treatment region. The intensity of the first beam may be the same as or different from the intensity of the second beam. For example, the energy of the first beam may be several megavolts (MV), this energy being greater than that of the second beam, which may be several kilovolts (kV).

The intensity of the radiation source (e.g., the first radiation source 113 and the second radiation source 111) can be changed in various ways. In a typical configuration, a linear accelerator associated with the radiation source (e.g., an accelerator that accelerates an electron towards a target to generate X-rays) may be operated in a pulsed mode, where radiation is produced in a very short pulse [each pulse lasting for example 3 microseconds], while the intensity remains constant during the pulse. For example, in order to achieve a change of (average) intensity, the duration of the pulse or the frequency of the pulses may be adjusted, such that when averaged over a period of time (for example 100 ms to 1 second), the intensity of the beam is changed. In typical embodiments, this averaged intensity is referred to as the "dose rate" or "output rate" of the linear accelerator and is typically expressed in Monitor Units (MU) per minute. An MU is a measure of machine radiation output. It is typically calibrated to a dose absorbed in a standardized phantom at a standardized position, under standardized conditions of irradiation. An MU rate is the number of MU that are produced per unit time. It is common to use the terms MU rate and dose rate interchangeably. However, in the strict sense, dose rate depends not only on the machine radiation output, but also the properties of the object to which radiation is imparted. In radiation therapy, the dose to be absorbed by a target tissue is prescribed. The radiation system 100 may produce a sequence of machine parameters to achieve the prescribed dose to be absorbed in the target tissue.

Thus, in a typical treatment plan, one of the main parameters which is optimized is the dose to be absorbed by tissues. Dose is linearly proportional to MU, as long as the exposed object and irradiation conditions do not change. As such, the dose rate will express the speed with which a certain dose is delivered. If all other parameters (including, but not limited to, beam shape or source position) remain constant, the dose rate itself is not very significant, since the spatial distribution of the dose in the target will not be affected by different dose rates. If, however, during the delivery, any other parameter such as the beam shape of the position of the source is modified, a change in dose rate will affect how the dose is distributed over the target volume. Under such conditions, the dose rate itself may also need to be optimized in order to achieve the correct dose distribution.

In some embodiments, the radiation delivery device 110 may further include a radiation detector 112 placed opposite to the second radiation source 111. In some embodiments, the radiation detector 112 may be mounted on a rotary ring 114. The radiation detector 112 may be configured to detect radiation. The second beam emitted from the second radiation source 111 may transmit through (or be absorbed by) the object and attenuate when passing through the object. The radiation detector 112 may detect and/or receive radiation associated with at least a portion of the attenuated or scattered second beam. The radiation system 100 (e.g., a processing device 140) may generate radiographs and CT images based on the received portion of the attenuated second beam. In some embodiments, the radiographs or the CT images may be obtained during a full rotation or a part of a rotation of the rotary ring (e.g., ½ rotation, ¼ rotation, $\frac{1}{10}^{th}$ rotation, $\frac{1}{20}^{th}$ rotation, $\frac{1}{100}^{th}$ rotation, etc.) The first radiation source 113, the second radiation source 111 and the radiation detector 112 may be mounted on a rotary ring 114. The rotary ring 114 may rotate around the object. The examples of the rotary ring 114 may be found elsewhere in this disclosure (e.g., rotary ring 440 illustrated in FIG. 4, rotary ring 630 illustrated in FIG. 6, rotary ring 740 illustrated in FIG. 7). The angular offset between first radiation source 113 and the second radiation source 111 (and/or the radiation detector 112) in a plane of the rotation of the rotary ring 114 may remain unchanged during the rotation of the rotary ring 114. In some embodiments, the radiation system 100 may include a gantry 116 to accommodate a bore 117 and a bed 115. Since the radiation system 100 is a combined therapy-imaging system, the bed 115 may be a scanning bed or a treatment couch. The rotary ring 114 may be rotatably connected to the gantry (e.g., the rotary ring 114 may rotate in X-Y plane but may not move in Z-direction when connected to the gantry 116). The bed 115 may be configured to support and/or transport the object (e.g., a patient) to the gantry 116 to be imaged and/or undergo radiotherapy.

It should be noted that the above descriptions of the radiation delivery device 110 are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. For example, the first radiation source 113 and the second radiation source 111 may both be treatment radiation sources. As another example, the first radiation source 113 and the second radiation source 111 may both be imaging radiation sources. Merely by way of example, a radiation detector may be mounted opposite to the first radiation source 113 on the rotary ring 114 configured to detect at least a portion of the first beam emitted from the first radiation source 113 (a portion of which may be attenuated when reaching the radiation detector). In some embodiments, the second radiation source 111 may be replaced by any other type of imaging device such as a computed tomography (CT) device, a magnetic resonance imaging (MRI) device, a positron emission tomography (PET) device, a single photon emission computed tomography (SPECT) device, or the like, or a combination thereof. More descriptions of the radiation delivery device 110 may be found elsewhere in the present disclosure (e.g., FIG. 4 and the descriptions thereof).

The network 120 may include any suitable network that can facilitate the exchange of information and/or data for the radiation system 100. In some embodiments, one or more components of the radiation system 100 (e.g., the radiation delivery device 110, the terminal(s) 130, the processing device 140, or the storage device 150) may communicate information and/or data with one or more other components of the radiation system 100 via the network 120. For example, the processing device 140 may obtain data corresponding to radiation signals from the radiation delivery device 110 via the network 120. As another example, the processing device 140 may obtain user instructions from the terminal(s) 130 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or a combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 120 may include one or more network access points. For example, the network 120 may include wired and/or wireless network access points such as base stations and/or internet exchange points through which one or more components of the radiation system 100 may be connected to the network 120 to exchange data and/or information.

The terminal(s) 130 may include a mobile device 131, a tablet computer 132, a laptop computer 133, or the like, or a combination thereof. In some embodiments, the mobile device 131 may include a smart home device, a wearable device, a smart mobile device, a virtual reality device, an augmented reality device, or the like, or a combination thereof. In some embodiments, the smart home device may include a smart lighting device, a control device of an intelligent electrical device, a smart monitoring device, a smart television, a smart video camera, an interphone, or the like, or a combination thereof. In some embodiments, the wearable device may include a smart bracelet, smart footgear, a pair of smart glasses, a smart helmet, a smartwatch, smart clothing, a smart backpack, a smart accessory, or the like, or a combination thereof. In some embodiments, the smart mobile device may include a smartphone, a personal digital assistant (PDA), a gaming device, a navigation device, a point of sale (POS) device, or the like, or a combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or a combination thereof. For example, the virtual reality device and/or the augmented reality device may include a Google Glass, an Oculus Rift, a Hololens, a Gear VR, etc. In some embodiments, the terminal(s) 130 may remotely operate the radiation delivery device 110. In some embodiments, the terminal(s) 130 may operate the radiation delivery device 110 via a wireless connection. In some embodiments, the terminal(s) 130 may receive information and/or instructions inputted by a user, and send the received information and/or instructions to the radiation delivery device 110 or the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted.

The processing device 140 may process data and/or information obtained from the radiation delivery device 110, the terminal(s) 130, and/or the storage device 150. For example, the processing device 140 may process data corresponding to radiation signals of one or more detectors obtained from the radiation delivery device 110 and reconstruct an image of the object. In some embodiments, the reconstructed image may be transmitted to the terminal(s) 130 and displayed on one or more display devices in the terminal(s) 130. The processing device 140 may obtain a treatment plan from the terminal (s), and/or the storage device 150 via the network 120. The treatment plan may correspond to a certain arrangement of the radiation delivery device 110 or components thereof. The processing device 140 may further adjust the treatment plan based on data and/or information received from the radiation delivery device 110 and may control the radiation delivery device 110 based on the adjusted treatment plan. In some embodiments, the processing device 140 may be a single server or a server group. The server group may be centralized or distributed. In some embodiments, the processing device 140 may be local or remote. For example, the processing device 140 may access information and/or data stored in the radiation delivery device 110, the terminal(s) 130, and/or the storage device 150 via the network 120. As another example, the processing device 140 may be directly connected to the radiation delivery device 110, the terminal(s) 130, and/or the storage device 150 to access stored information and/or data. As a further example, the processing device 140 may be integrated into the radiation delivery device 110. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal(s) 130 and/or the processing device 140. For example, the storage device 150 may store a treatment plan and/or an adjusted treatment plan. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or a combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or a combination thereof.

In some embodiments, the storage device 150 may be connected to the network 120 to communicate with one or more components of the radiation system 100 (e.g., the processing device 140, the terminal(s) 130, etc.). One or more components of the radiation system 100 may access the data or instructions stored in the storage device 150 via the network 120. In some embodiments, the storage device 150 may be directly connected to or communicate with one or more components of the radiation system 100 (e.g., the processing device 140, the terminal(s) 130, etc.). In some embodiments, the storage device 150 may be part of the processing device 140.

FIG. 2 is a schematic diagram illustrating hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data obtained from the radiation delivery device 110, the terminal(s) 130, the storage device 150, and/or any other component of the radiation system 100. In some embodiments, the processor 210 may perform instructions obtained from the terminal(s) 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof. Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the radiation delivery device 110, the terminal 130, the storage device 150, or any other component of the radiation system 100. In some embodiments, the storage 220 may include a mass storage device, a removable storage device, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for reducing or removing one or more artifacts in an image.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation delivery device 110, the terminal 130, or the storage device 150. The connection may be a wired connection, a wireless connection, or combination of both that enables data transmission and reception. The wired connection may include an electrical cable, an optical cable, a telephone wire, or the like, or a combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
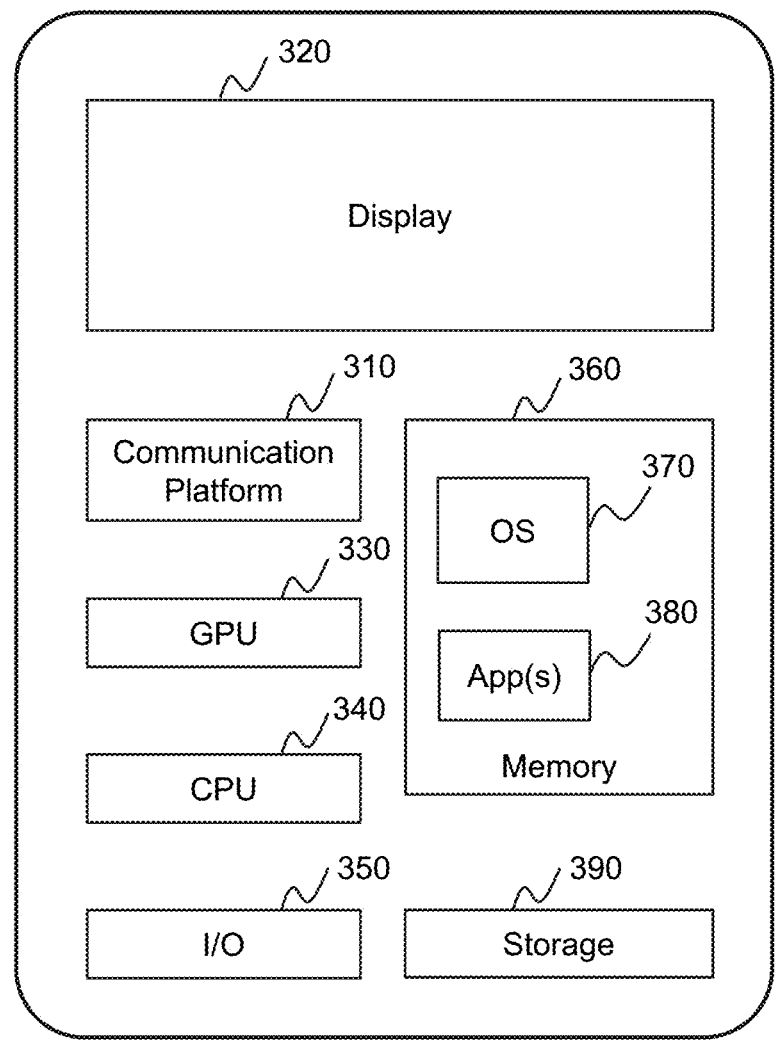
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to radiation systems for treatment and imaging as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result, the drawings should be self-explanatory.

Figure 4:
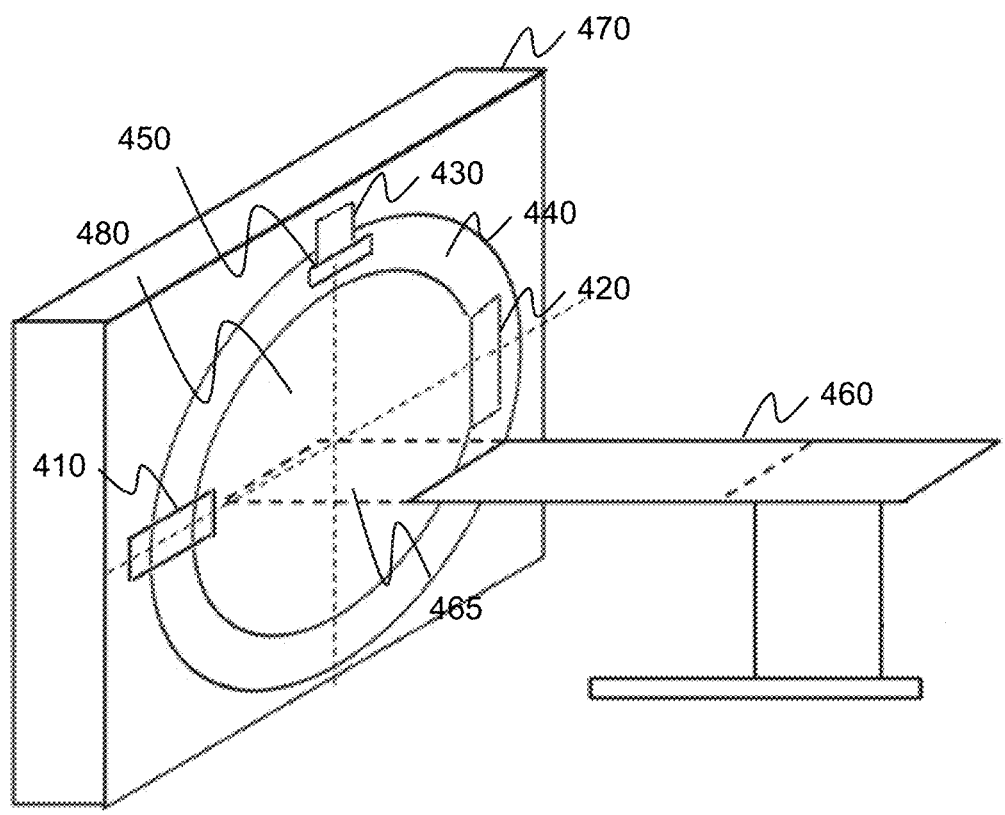
FIG. 4 is a schematic diagram illustrating an exemplary radiation delivery device according to some embodiments of the present disclosure.

FIG. 4 is a schematic diagram illustrating an exemplary radiation delivery device according to some embodiments of the present disclosure. As shown in FIG. 4, the radiation delivery device 400 may include a treatment radiation source 430 (also referred to as a first radiation source), a multi-leaf collimator (MLC) 450, an imaging radiation source 410 (also referred to as a second radiation source), and a radiation detector 420. The MLC may contain leaves that move continuously or assume discrete positions. The MLC may contain leaves that are "binary" in that a leaf may assume only closed (radiation-attenuating) and open (radiation-transmitting) states. The radiation delivery device 400 may be an exemplary embodiment of the radiation delivery device 110 but shall not be considered as the only possible configuration of the radiation delivery device 110. People having ordinary skill in the art may, under the teaching of the present disclosure, add, delete, or amend any components in the radiation delivery device 110 or 400. Such amendment is also under the protection scope of the present application. Unless otherwise stated, components with the same names in the radiation delivery device 110 and the radiation delivery device 400 may have the same or similar functions.

The imaging radiation source 410, the treatment radiation source 430, the MLC 450, and the radiation detector 420 may be mounted on a rotary ring 440. In some embodiments, the radiation delivery device 400 may include a gantry 470 to accommodate a bore 480 and a bed 460. The bed 460 may be configured to support the object (e.g., a patient) and/or transport the object to the gantry 470, where the object may be to be imaged and/or undergo radiotherapy.

The treatment radiation source 430 may be configured to deliver a treatment beam toward a treatment region of the object. For example, the process of delivering the treatment beam toward the treatment region of the object may refer to a radiotherapy (RT) treatment. The treatment region may include a cell mass, a tissue, an organ (e.g., a prostate, a lung, a brain, a spine, a liver, a pancreas, a breast, etc.), or a combination thereof. In some embodiments, the treatment region may include a tumor, an organ with a tumor, or a tissue with a tumor. The treatment beam may include a particle beam, a photon beam, an ultrasound beam (e.g., a high intensity focused ultrasound beam), or the like, or a combination thereof. The particle beam may include a stream of neutrons, protons, electrons, heavy ions, or the like, or a combination thereof. The photon beam may include an X-ray beam, a γ-ray beam, an α-ray beam, a β-ray beam, an ultraviolet beam, a laser beam, or the like, or a combination thereof. The shape of the X-ray beam may be a line, a narrow pencil, a narrow fan, a fan, a cone, a wedge, or the like, or a combination thereof. The energy level of the treatment beam may be suitable for radiotherapy. For example, an X-ray beam delivered by the treatment radiation source 430 may have an energy of the megavoltage (MV) level. Merely by way of example, the energy of the X-ray beam emitted by the treatment radiation source 430 may be 6 MV.

In some embodiments, the treatment radiation source 430 may be activated and emit a treatment beam to the treatment region according to a predetermined treatment plan. The predetermined treatment plan may include parameters associated with one or more radiation segments. The radiation segment may be an arc-shaped segment on the rotation trajectory of the rotary ring at which treatment radiation source 430 delivers the treatment beam to the treatment region. The parameters associated with the radiation segments may include a desired segment shape (e.g., a desired shape of the aperture formed by the MLC 450), a desired segment intensity (e.g., a desired segment MU value, a desired segment MU rate), a desired segment angle range, and/or a desired relative position of the object relative to the rotary ring 440. For example, the treatment radiation source 430 may start the delivery of the treatment beam to the treatment region when a desired segment angle range is reached during the rotation of the rotary ring 440 based on the treatment plan. In some embodiments, the intensity of the treatment radiation source 430, the position of the bed 460, and/or the shape of the leaves in the MLC 450 (which corresponds to the shape of the aperture formed by the MLC 450) may also be adjusted based on the predetermined treatment plan. During the treatment, the motion of the treatment region may be tracked, and the real-time location of the treatment region may be determined by a processing device 140 based on image data generated by the imaging radiation source 410 and the radiation detector 420. In some embodiments, the treatment radiation source 430 may include a linear accelerator (LINAC) configured to generate the treatment beam.

In some embodiments, the radiation delivery device 400 may further include a treatment beam detector (not shown in the figure) placed on the rotary ring 440 opposite to the treatment radiation source 430. The treatment beam detector may be configured to detect and/or receive radiation associated with the beams (e.g., X-ray treatment beams) emitted from the treatment radiation source 430 (which may be attenuated). The treatment beam detector may detect and/or receive radiation associated with the beams emitted from the treatment radiation source 430 during and/or before a radiotherapy operation performed by the treatment radiation source 430. For example, during the radiotherapy operation performed by the treatment radiation source 430, the treatment beam detector may detect the radiation associated with the beams emitted from the treatment radiation source 430 and monitor the condition (e.g., the radiation dose) of the radiotherapy. As another example, before the radiotherapy operation, the treatment radiation source 430 may deliver a pre-treatment beam, and the treatment beam detector may detect radiation associated with at least portion of the pre-treatment beam for calibration (e.g., a calibration of the radiation dose). In some embodiments, the shape of the treatment beam detector may be flat, arc-shaped, circular, or the like, or a combination thereof. For example, the treatment beam detector may be a flat panel detector configured to detect radiation emitted by the treatment radiation source 430 after attenuation by the object.

The imaging radiation source 410 and the radiation detector 420 (which are also referred to an imaging assembly collectively) may be configured to provide image data for generating an image of the treatment region (or an imaging region that overlaps with the treatment region), which may be used to determine a real-time location of the treatment region, and/or track the motion of the treatment region during a radiotherapy operation performed by the treatment radiation source 430. In some embodiments, the location of the treatment region of the object may change with time due to various motions, for example, cardiac motion (and its effect on other organs), respiratory motion (of the lungs and/or the diaphragm, and its effect on other organs), blood flow and motion induced by vascular pulsation, muscles contraction and relaxation, secretory activity of the pancreas, or the like, or a combination thereof. The location of the treatment region may be monitored based on an image (e.g., a CT image, a cone beam computed tomography (CBCT) image, an MRI image, a PET image, a PET-CT image) of the object generated according to the image data acquired by the imaging assembly before, during, and/or after the radiotherapy operation.

In some embodiments, the imaging radiation source 410 may be configured to emit an imaging beam to the object. The imaging beam may include a particle beam, a photon beam, or the like, or a combination thereof. The particle beam may include a stream of neutrons, protons, electrons, heavy ions, or the like, or a combination thereof. The photon beam may include an X-ray beam, a γ-ray beam, an α-ray beam, a β-ray beam, an ultraviolet beam, a laser beam, or the like, or a combination thereof. The shape of the X-ray beam may be a line, a narrow pencil, a narrow fan, a fan, a cone, a wedge, a tetrahedron, or the like, or a combination thereof. For example, the radiation source may be a cone beam computed tomography (CBCT) radiation source and the imaging beam may be a cone beam. In some embodiments, the cone angle of the imaging beam may be larger than the cone angle of the treatment beam. The cone angle may be defined as an angle formed between two lines connecting an apex and two end points on a diameter of a cross-section of a cone-shaped beam. More particularly, when the rotary ring 440 rotates, the space covered by the imaging beam may be larger than the space covered by the treatment beam. The energy level of the imaging beam may be suitable for imaging. In some embodiments, the energy level of the imaging beam may be the same as or different from that of the treatment beam generated by the treatment radiation source 430. For example, an X-ray beam delivered by the imaging radiation source 410 may have an energy of a kilovoltage (kV) level. Merely by way of example, the energy of the X-ray beam may be 90 kV.

Key to the teachings contained herein is the concept of a cone beam X-ray imaging system, and cone beam computed tomography (CBCT). In the vast majority of X-ray imaging systems, X-rays are produced by a Bremsstrahlung process in which electrons are incident on an X-ray target. The electrons lose kinetic energy in the target, and this energy is converted to heat and X-rays. X-rays are emitted in all directions. In reflection targets (such as those used in the vast majority of diagnostic X-ray imaging systems), the X-rays emitted in the direction of the target are substantially absorbed by the target. The X-rays that leave the target are emitted over a wide solid angle. These rays usually leave the X-ray tube through an exit window that is substantially transparent to x-rays. When the exit window is circular, the shape of the beam is a true cone. However, most systems (e.g., in planar radiography applications) collimate the beam to a rectangular cross section. Nevertheless, such a beam is also termed a cone beam. In single slice CT systems, the cone beam is much more narrowly collimated along the long axis of the patient (direction that patient couch travels) than lateral axis (usually along the plane of rotation of the imaging system). Such a beam is typically referred to as a fan beam, rather than a cone beam, even though the beam may, before collimation, have assumed the form of a cone. In multislice CT (and helical scan implementations of multislice CT), the detector typically has larger axial extent than in the fan beam CTs. However, it is not typical to refer to the beam of a multislice CT as a cone beam, since it is much more substantially collimated in the axial direction as compared to the lateral direction.

Linear accelerator X-ray sources (e.g., the treatment radiation source 430 and the imaging radiation source 410) almost universally rely on Bremsstrahlung from transmission targets to generate photon beams. Like reflection sources, transmission targets also generate X-rays that travel in all directions. However, the target is itself substantially transparent to the emerging X-rays. The higher the energy of the incident electrons, the more concentrated is the flux of photons in the forward (transmission) direction (directions more closely aligned with that of the original electron beam). The emerging photon beams are almost always collimated by a conical primary collimator, forming substantially a cone beam. However, this cone beam may be further collimated. In most systems, collimation is achieved by rectangular jaws and/or a 2D multileaf collimator. In the present disclosure, such further collimated beams are also termed cone beams. In contrast, a minority of radiation therapy systems, such as that described in U.S. Pat. No. 5,548,627 (which describes the basis of the Tomotherapy line of radiation therapy systems), are designed to produce a beam "only within the gantry plane." The gantry plane in such systems is substantially narrower than the lateral extent of the patient and the treatment field. This narrow collimation along the long axis of the patient, by analogy with the fan beam CT and multislice CT cases, means that such a beam is not considered a cone beam by people having ordinary skills in the art of x-ray imaging and therapy systems. In fan beam CT, multislice CT, and tomotherapy, the patient support is almost always translated along the long axis of the patient in order to image and/or treat all volumes of interest. In cone beam CT, and therapy with 2D (collimated) cone beams, the patient support is almost never moved to accomplish imaging and/or treatment of volumes of interest.

In view of the above, the term "cone angle" as applied to a collimated cone beam, is taken to be the angle subtended at the source of the collimated beam, by the edges of the collimated field, in the particular direction along with the field is collimated. Understanding of the teachings contained herein require the disambiguation of the concept of a "CT detector" (e.g., the radiation detector 420). For CBCT, flat panel detectors are normally used. These detectors almost always have a relatively large area (e.g. 8 in×8 in, 16×16 in, 40 cm×30 cm), and low aspect ratio (ratios of length to width such as 1:1 and 4:3). In contrast, CT detectors may not be flat, and have much higher aspect ratios, where the arc length of the detector in the plane of rotation (lateral extent, or fan angle) greatly exceeds the axial dimension (and subjected axial angle from the source) of the detector. In most cases, CT detectors are arranged along an isocentric arc at the same radius as the source. In most cases, CT detector assemblies include a collimator that collimates the detector elements to the source. In effect, each axial detector row is collimated to a fan beam.

The radiation detector 420 may be configured to detect or receive radiation associated with at least a portion of the imaging beam emitted from the imaging radiation source 410 to generate imaging data (e.g., projection data). The imaging data may be transmitted to the processing device 140 for further processing. The processing device 140 may reconstruct an image of the object or a portion thereof based on the imaging data. The location of the treatment region of the object may be determined based on the image.

In some embodiments, the radiation detector 420 may include one or more detector units. A detector unit may include a scintillator layer (e.g., a cesium iodide scintillator layer, a gadolinium oxysulfide scintillator layer), a gas detector, etc. In some embodiments, the detector units may be arranged in a single row, two rows, or any other number of rows. Merely by way of example, the radiation detector 420 may be a CT detector configured to detect X-rays (e.g., radiation emitted by the imaging radiation source 410 after attenuation by the object). The shape of the radiation detector 420 may be flat, arc-shaped, circular, or the like, or a combination thereof. For example, the radiation detector 420 may be a flat panel detector. In some embodiments, a dual layer detector, or photon counting detector, may be employed to obtain energy information from the impinging X-ray beam.

The gantry 470 may be configured to support one or more components of the radiation delivery device 110 (e.g., the treatment radiation source 430, the treatment beam detector, the imaging radiation source 410, the radiation detector 420). In some embodiments, the gantry 470 may include a movement restriction component configured to limit the movement (e.g., the movement along the Z-direction) of the rotary ring 440. The movement restriction component may also protect one or more components of the radiation delivery device 400 from swinging out from the radiation delivery device 400 during the movement of the rotary ring 440. Merely by way of example, the movement restriction component may be a housing outside the rotary ring 440 (and/or the components thereof). The movement restriction component may be attached to the inner surface of the gantry 470.

In some embodiments, the radiation delivery device 400 may further include a cooling device (not shown in the figure). The cooling device may be configured to produce, transfer, deliver, channel, or circulate a cooling medium to the radiation delivery device 400 to absorb heat produced by the radiation delivery device 400 (e.g., the radiation detector 420) during an imaging procedure and/or radiotherapy operation. The bed 460 may be configured to support and/or transport the object (e.g., a patient) to be imaged and/or undergo radiotherapy.

Figure 5:
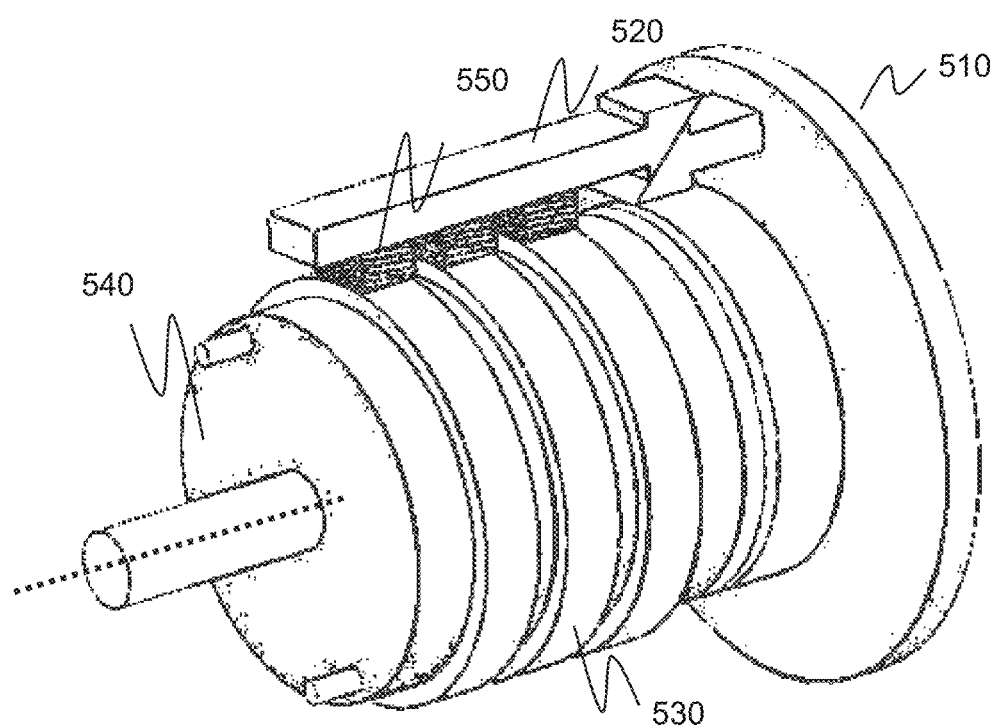
FIG. 5 is a schematic diagram illustrating an exemplary slip ring according to some embodiments of the present disclosure.

FIG. 5 is a schematic diagram illustrating an exemplary slip ring according to some embodiments of the present disclosure. As shown in FIG. 5, the slip ring 500 may include a stationary portion 510, a connector 520, and a rotary portion 540. In some embodiments, the stationary portion 510 may be fixed, and the rotary portion 540 may rotate around its center axis (i.e., the dotted line). The rotary portion 540 and the stationary portion 510 may be connected to each other via the connector 520. The stationary portion 510 may be electrically connected to a power supply (e.g., a three-phase electric mains). The stationary portion 510 may extract electricity from the power supply and transmit the electricity via cables inside the stationary portion 510 to three conducting ports 550 (which may correspond to a live cable, a neutral cable, and a ground cable, respectively). The three conducting ports 550 may touch and be electrically connected to three conducting bars 530 mounted on the surface of the rotary portion 540, respectively. The conducting bars may be continuously connected to the corresponding conducting bars regardless of whether the rotary portion 540 is rotating or at rest. In some embodiments, the rotary portion 540 may be connected to a rotary ring (e.g., the rotary ring 114, the rotary ring 440). As such, the slip ring 500 may enable the rotary ring 114 to rotate continuously around the object and supply power to the components mounted on the rotary ring 114 (e.g., the first radiation source 113, the second radiation source 111 and/or the radiation detector 112). The slip ring 500 may also transmit one or more of the following data: control data to and from the linear accelerator, control and image data to and from the imaging detectors paired within the first radiation source and second radiation source, control data (such as exposure, beam energy and x-ray pulse timing) to and from the second radiation source.

In some embodiments, the slip ring may be replaced by any kind of rotatable component, such as a gear, a reel, a rotation shaft, etc. For example, a rotation of the rotary ring 114 is driven via at least one of a slip ring, a gear, a reel, or a rotation shaft. In a case that the kind of rotatable component cannot supply power to the rotary ring 630, the power of the rotary ring 630 and/or components thereof (e.g., the imaging source 410, the radiation detector 420, and/or the treatment source 430) may be supplied by a battery or supercapacitor placed inside the rotary ring 630. As another example, rotary ring 630 and/or components thereof may be charged by a wireless charging device, or the like.

Figure 6:
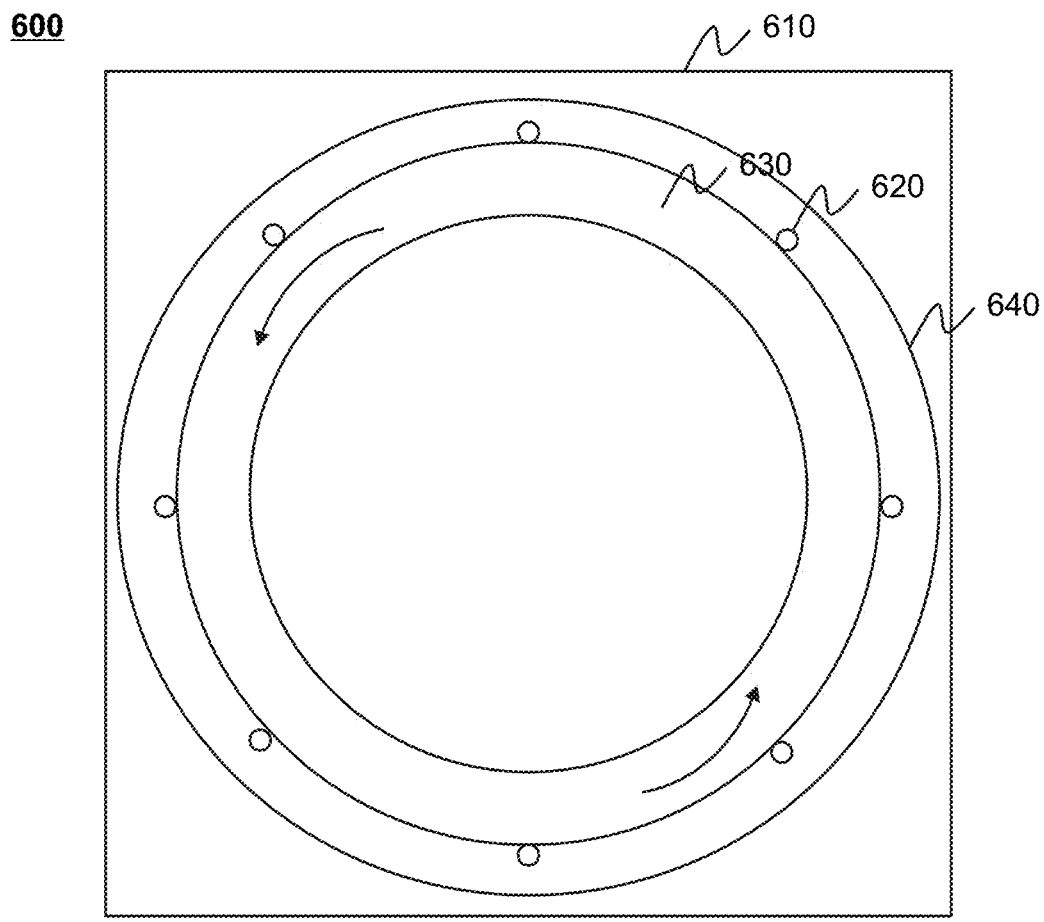
FIG. 6 is a schematic diagram illustrating an exemplary connection of a rotary ring and a slip ring according to some embodiments of the present disclosure.

FIG. 6 is a schematic diagram illustrating an exemplary connection of a rotary ring and a slip ring according to some embodiments of the present disclosure. As shown in FIG. 6, radiation delivery device 600 may include a gantry 610, a connector 620, and a stationary portion 640 of a slip ring, and a rotary ring 630. The stationary portion 640 may be fixedly connected to the gantry 610 and may remain at rest when the rotary portion (or the rotary ring 630) rotates. The rotary ring 630 may be mounted on a rotary portion (not shown in the figure). In some embodiments, the connector 620 may each include three conducting ports (similar to the conducting ports 550). The rotary portion (or the rotary ring 630) may include three conducting bars around its circumference. Conducting ports of the connector 620 may touch and be electrically connected to the conducting bars at respective locations. The connector 620 can both hold and supply power to the rotary ring 630.

Figure 7A:
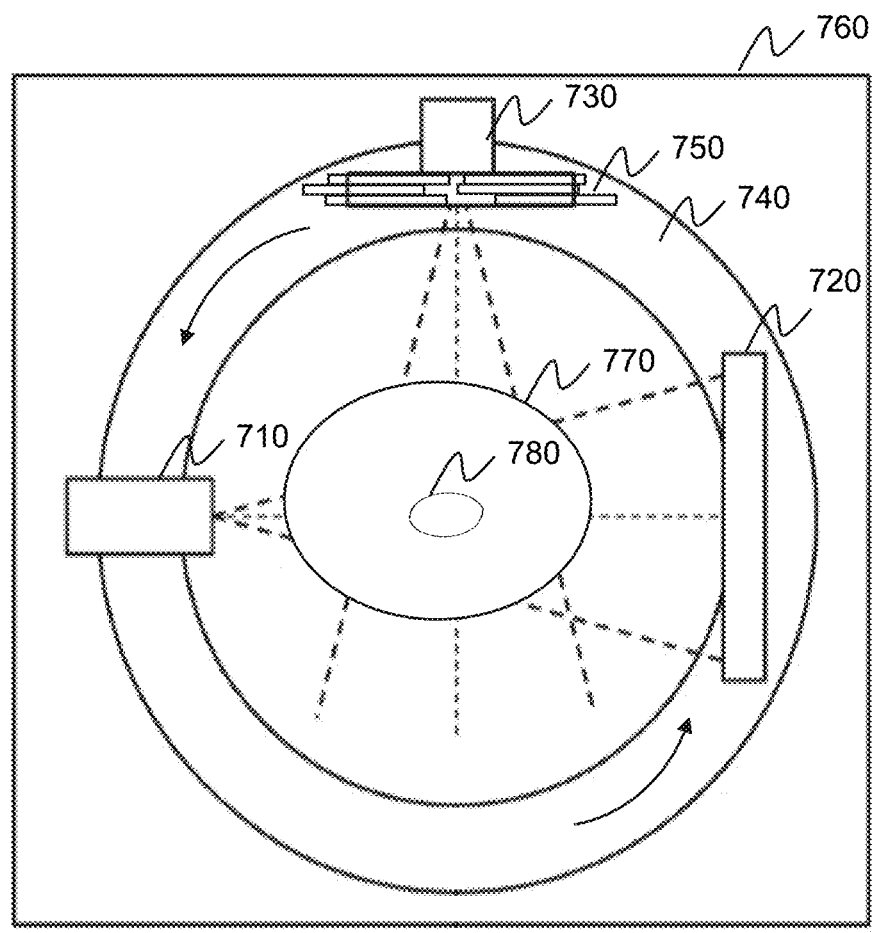
FIG. 7A and FIG. 7B are schematic diagrams illustrating different configurations of an exemplary radiation delivery device according to some embodiments of the present disclosure.
Figure 7B:
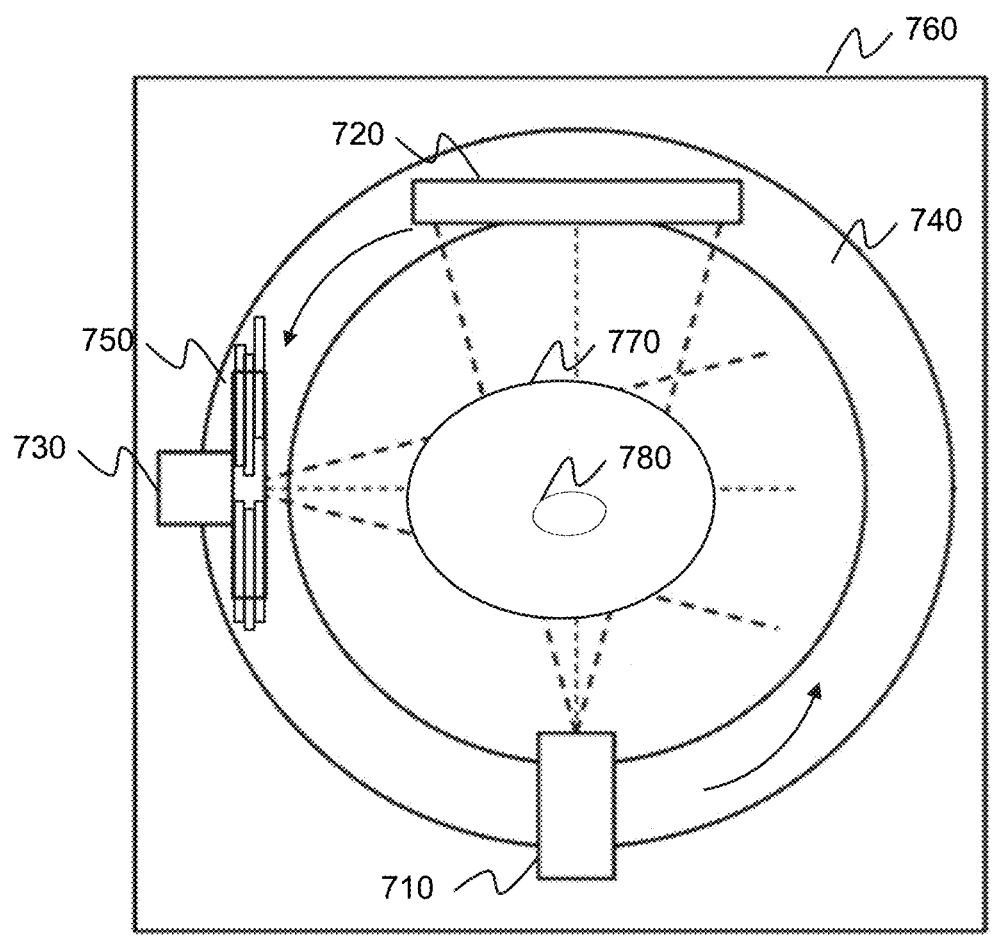

FIG. 7A and FIG. 7B are schematic diagrams illustrating different configurations of an exemplary radiation delivery device according to some embodiments of the present disclosure. In some embodiments, FIG. 7A and FIG. 7B may correspond to the same radiation delivery device 700 before and after a rotation, respectively. In some embodiments, the radiation delivery device 700 may be an exemplary embodiment of the radiation delivery device 110 but shall not be considered as the only possible configuration of the radiation delivery device 110. People having ordinary skill in the art may, under the teaching of the present disclosure, add, delete, or amend any components in the radiation delivery device 110 or 700. Such amendment is also under the protection scope of the present application. Unless otherwise stated, components with same names in the radiation delivery device 110 and the radiation delivery device 700 may have similar functions.

As shown in FIG. 7A, the radiation delivery device 700 may include a treatment radiation source 730 (also referred to as a first radiation source), an imaging radiation source 710 (also referred to as a second radiation source), a radiation detector 720, a rotary ring 740, an MLC 750 and a gantry 760. An object 770 (e.g., a patient) may lie on a bed (not shown in the figure). The object 770 may include a tumor region 780 and be scanned and/or undergo radiotherapy. In some embodiments, the treatment radiation source 730 may emit a treatment beam toward a treatment region of an object 770. The MLC 750 may include a plurality of leaves that form an aperture. The aperture may modify the shape of the treatment beam. The MLC 750 may be moved during the rotation of the rotary ring 740 according to a treatment plan.

The imaging radiation source 710 may emit an imaging beam toward an imaging region of the object 770. The radiation detector 720 may receive an attenuated imaging beam that transmits through the imaging region, and generate image data associated with the imaging region. In order to obtain an image data of the treatment region of the object 770, the imaging region may include or overlap with the treatment region. As used herein, a treatment region (or an imaging region) may be defined as a region that the treatment beam impinges upon the object 770. Ideally, the treatment region associated with the radiotherapy may coincide with the tumor region 780 of the object 770.

In some embodiments, the radiation delivery device 700 may operate based on a treatment plan. The treatment plan may include a plurality of parameters associated with one or more radiation segments. The radiation segment may be an arc-shaped segment on the rotation trajectory of the rotary ring at which treatment radiation source 730 delivers the treatment beam to the treatment region. The parameters associated with the one or more radiation segments may include a desired segment shape, a desired segment intensity (e.g., a desired segment MU value, a desired segment MU rate), a desired segment angle range, and/or a desired relative position of the object relative to the rotary ring 740. In some embodiments, when the rotary ring 740 rotates, the imaging radiation source 710 may emit an imaging beam during the whole or most of the 360 degrees (also referred to as a full rotation) of the rotation of the rotary ring 740, and the radiation detector 720 may detect radiation associated with the imaging beam. However, the treatment radiation source 730 may operate only at the desired segment angle ranges (e.g., from 0 degrees to 20 degrees, from 65 degrees to 90 degrees) based on the treatment plan. When the treatment radiation source 730 reaches a radiation segment, the MLC 750 may also change the shape of the aperture it forms based on desired segment shape of the treatment plan.

In some embodiments, FIG. 7A illustrates a configuration of a radiation delivery device 700 before the rotation of the rotary ring 740. FIG. 7B illustrates a configuration of the same radiation delivery device 700 after a 90 degrees rotation of the rotary ring 740. It may be noted from FIG. 7A and FIG. 7B that the angular offset between the treatment radiation source 730 and the imaging radiation source 710 (and/or the radiation detector 720) in the plane of rotation of the rotary ring 740 may remain unchanged during the rotation of the rotary ring 740. It may be understood that the rotary ring 740 may continue to rotate, and when the rotary ring 740 rotates for 360 degrees (i.e., a rotary ring rotates a full rotation), the components of the radiation delivery device 700 may return to their initial positions similar to their respective positions illustrated in FIG. 7A.

In some embodiments, a full rotation in the present disclosure may generally refer to a rotation of 360 degrees (of the rotary ring). However, the imaging or the treatment process disclosed in the present application may only last for a portion of the 360 degrees. Hence, the full rotation may also refer to a rotation of certain degrees less than or equal to 360 degrees (e.g., 270 degrees, 300 degrees) that the imaging or the treatment process disclosed in the present application is finished or the detected treatment result or image data is sufficient for further processing.

Figure 8:
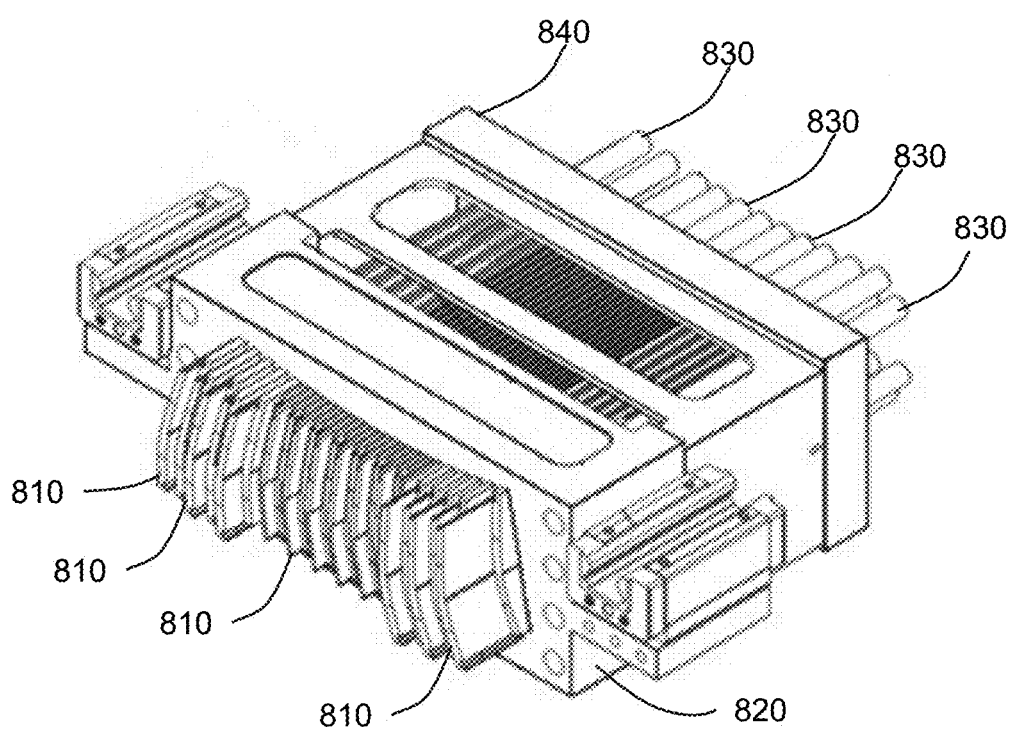
FIG. 8 is a schematic diagram illustrating an exemplary multi-leaf collimator (MLC) according to some embodiments of the present disclosure.

FIG. 8 is a schematic diagram illustrating an exemplary multi-leaf collimator (MLC) according to some embodiments of the present disclosure. The multi-leaf collimator (MLC) 800 may include a plurality of leaves 810, a rail box 820, a plurality of motors 830, and a housing 840. Each of the motors 830 may control the movement (e.g., a linear movement) of a corresponding leave 810. The plurality of motors 830 may be controlled by a processing device (e.g., the processing device 140) such that they may move the plurality of leaves in a controlled way (e.g., based on a treatment plan) to form a desired shape of the aperture.

Figure 9:
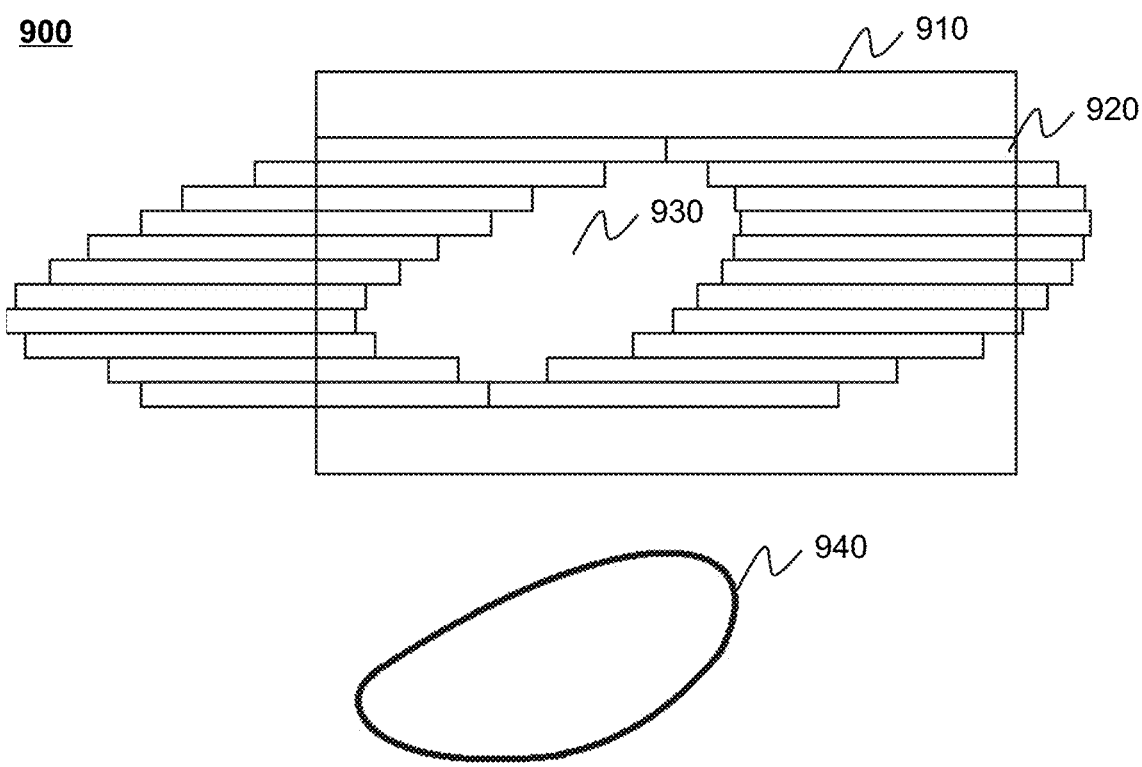
FIG. 9 is schematic diagram illustrating a shape of an exemplary aperture formed by an MLC and a corresponding treatment region.

FIG. 9 is a schematic diagram illustrating a shape of an exemplary aperture formed by an MLC and corresponding treatment region. In some embodiments, the MLC 900 may be placed between a treatment radiation source (e.g., the first radiation source 113, the treatment radiation source 430, the treatment radiation source 730) and a bore (e.g., bore 117). The MLC 900 may modify the shape of the beam emitted from the radiation source to a shape similar to the aperture 930 formed by the leaves 920 of the MLC. In some embodiments, the processing device 140 may obtain a treatment plan. The treatment plan may include a desired segment shape of a radiation segment. The desired segment shape may correspond to the shape of desired treatment region 940. The leaves 920 of the MLC may be moved based on the treatment plan such that the aperture 930 formed by the leaves 920 may modify the shape of the beam emitted from the radiation source. The modified beam may be delivered toward and match (or approximately match) the desired treatment region 940.

Figure 10:
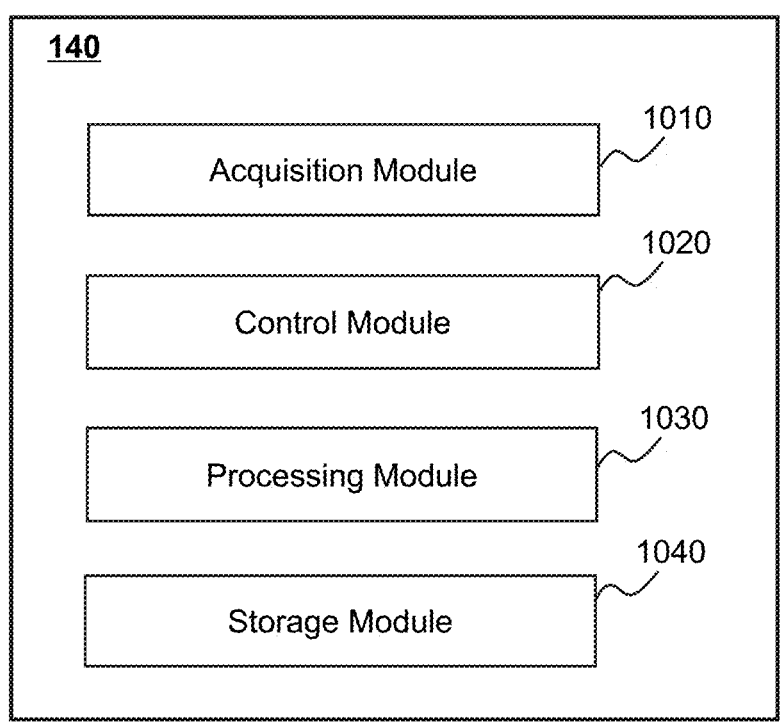
FIG. 10 is a block diagram illustrating an exemplary processing device according to some embodiments of the present disclosure.

FIG. 10 is a block diagram illustrating an exemplary processing device according to some embodiments of the present disclosure. The processing device 140 may include an acquisition module 1010, a control module 1020, a processing module 1030, and a storage module 1040. At least a portion of the processing device 140 may be implemented on a computing device as illustrated in FIG. 2 or a mobile device as illustrated in FIG. 3.

The acquisition module 1010 may acquire imaging data. In some embodiments, the acquisition module 1010 may acquire the imaging data (e.g., CT imaging data) from the radiation delivery device 110, the terminal 130, the storage device 150, and/or an external data source (not shown). In some embodiments, the imaging data may include raw data (e.g., projection data). For example, the imaging data (e.g., projection data) may be generated based on detected imaging beams at least some of which have passed through an object being imaged and treated in the radiation delivery device 110. In some embodiments, the acquisition module 1010 may acquire one or more instructions for processing the imaging data. The instructions may be executed by the processor(s) of the processing device 140 to perform exemplary methods described in this disclosure. In some embodiments, the acquired imaging data may be transmitted to the storage module 1040 to be stored.

In some embodiments, the acquisition module 1010 may acquire a treatment plan for an object. The treatment plan may include parameters associated with at least one radiation segments. The radiation segment may be an arc-shaped segment on the rotation trajectory of the rotary ring at which the treatment radiation source delivers the treatment beam to the treatment region. The acquisition module 1010 may acquire the treatment plan from one or more components of the radiation system 100 (e.g., the storage device 150, the terminal 130), or from an external source (e.g., an electronic medical record, a medical database) via the network 120.

The control module 1020 may control operations of the acquisition module 1010, the storage module 1040, the processing module 1030 (e.g., by generating one or more control parameters), the radiation delivery device 110, or the like, or a combination thereof. For example, the control module 1020 may cause the acquisition module 1010 to acquire imaging data, the timing of the acquisition of the imaging data, etc. As another example, the control module 1020 may cause the processing module 1030 to process imaging data acquired by the acquisition module 1010. In some embodiments, the control module 1020 may control the operation of the radiation delivery device 110. For example, the control module 1020 may cause the radiation delivery device 110 (e.g., the treatment assembly) to start, pause, stop, and/or resume the delivery of the imaging beam and/or the treatment beam to the object. As another example, the control module 1020 may cause the radiation delivery device 110 to adjust the radiation dose of the imaging beam or treatment beam to the object.

In some embodiments, the control module 1020 may receive a real-time instruction from an operator or retrieve a predetermined instruction provided by a user (e.g., a doctor) to control one or more operations of the radiation delivery device 110, the acquisition module 1010, and/or the processing module 1030. For example, the control module 1020 may adjust the acquisition module 1010 and/or the processing module 1030 to generate one or more images of an object according to the real-time instruction and/or the predetermined instruction. As another example, the control module 1020 may cause the radiation delivery device 110 to adjust the treatment beam delivered to the object according to the real-time instruction and/or the predetermined instruction. As a further example, the control module 1020 may gate and/or adjust the delivery of the treatment beam of the treatment assembly based on real-time monitoring of the location of the treatment region of the object according to the generated image(s). As still a further example, the control module 1020 may cause the position of the bed 115 and/or the treatment assembly (e.g., the first radiation source 113) to be adjusted according to the generated image(s), so that the treatment beam may target the treatment region of the object. In some embodiments, the control module 1020 may communicate with one or more other modules of the processing device 140 for exchanging information and/or data.

The processing module 1030 may process information provided by various modules of the processing device 140. The processing module 1030 may process imaging data acquired by the acquisition module 1010, imaging data retrieved from the storage module 1040 and/or the storage device 150, etc. In some embodiments, the processing module 1030 may reconstruct one or more images based on the imaging data according to a reconstruction technique. The reconstruction technique may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or a combination thereof. The reconstruction technique may be applied over a limited angular range to perform tomosynthesis imaging. In some embodiments, the processing module 1030 may perform pre-processing on the imaging data before the reconstruction. The pre-processing may include, for example, imaging data normalization, imaging data smoothing, imaging data suppressing, imaging data encoding (or decoding), denoising, etc.

In some embodiments, based on one or more reconstructed images of an object including a treatment region, the processing module 1030 may determine a change of location or shape of the treatment region. In some embodiments, the processing module 1030 may determine, based on the images and the analysis thereof, whether any change or adjustment is needed with respect to the treatment plan, and/or determine the needed adjustment. According to the determined adjustment, the control module 1020 may cause the adjustment to be implemented. For instance, the control module 1020 may cause the radiation delivery device 110 to deliver an adjusted treatment beam or adjust a position of the object. For example, the processing module 1030 may transmit the motion information of the treatment region to the control module 1020. The control module 1020 may accordingly control the radiation delivery device 110 to adjust the delivery of the treatment beam by, for example, pausing the delivery and/or changing the position of the source of the treatment beam. As another example, the control module 1020 may accordingly control the radiation delivery device 110 to adjust the position of the object with respect to the treatment beam.

In some embodiments, the delivery of a treatment plan may be monitored and/or adjusted real time. For instance, based on the imaging data the imaging scan components and/or the acquisition module 1010 acquires (e.g., real time), the processing module 1030 may automatically generate and/or analyze images to monitor the location of the treatment region of the object, and/or assess the change of the location of the treatment region, on the basis of which the processing module 1030 may determine how to proceed further with the treatment plan (e.g., to continue the radiotherapy as planned, to continue the radiotherapy with a revised plan, or to terminate the radiotherapy, etc.). The processing module 1030 may determine the location of the treatment region based on the generated image(s). In some embodiments, the monitoring, assessment, and/or adjustment may be performed semi-automatically with the input of a user. For instance, based on the imaging data the imaging scan components and/or the acquisition module 1010 acquires (e.g., real time), the processing module 1030 may generate one or more images and send them to be presented on a terminal 130 (e.g., a display) so that the user may analyze the images and provide an instruction as to how to proceed further with the treatment plan (e.g., to continue the radiotherapy as planned, to continue the radiotherapy with a revised plan, or to terminate the radiotherapy, etc.). The processing module 1030 may determine accordingly if any adjustment in the treatment plan is needed. If the change of location or shape of the target region or is within a threshold, the processing module 1030 may determine the adjustment automatically and send it to, e.g., the control module 1020, to be implemented. In some embodiments, a notification may be generated when the processing module 1030 makes such a determination. If the change of location or shape of the target region is not within a threshold, the processing module 1030 may generate a notification to, e.g., the user (e.g., the doctor), to seek instructions from the user as to how to proceed further.

The storage module 1040 may store imaging data, control parameters, processed imaging data, treatment plan, adjusted treatment plan, or the like, or a combination thereof. In some embodiments, the storage module 1040 may store one or more programs and/or instructions that may be executed by the processor(s) of the processing device 140 to perform exemplary methods described in this disclosure. For example, the storage module 1040 may store program(s) and/or instruction(s) that can be executed by the processor(s) of the processing device 140 to acquire imaging data of an object, reconstruct one or more images based on the imaging data, determine an ROI in the image(s), detect a change of location or shape of a treatment region of the object based on the image(s), revise the delivery of the treatment beam to the treatment region, and/or adjust the position of the object relative to the treatment beam based on the detected change of location or shape of the treatment region.

In some embodiments, one or more modules illustrated in FIG. 10 may be implemented in at least part of the radiation system 100 as illustrated in FIG. 1. For example, the acquisition module 1010, the control module 1020, the processing module 1030, and/or the storage module 1040 may be implemented via the processing device 140 and/or the terminal 130.

Figure 11:
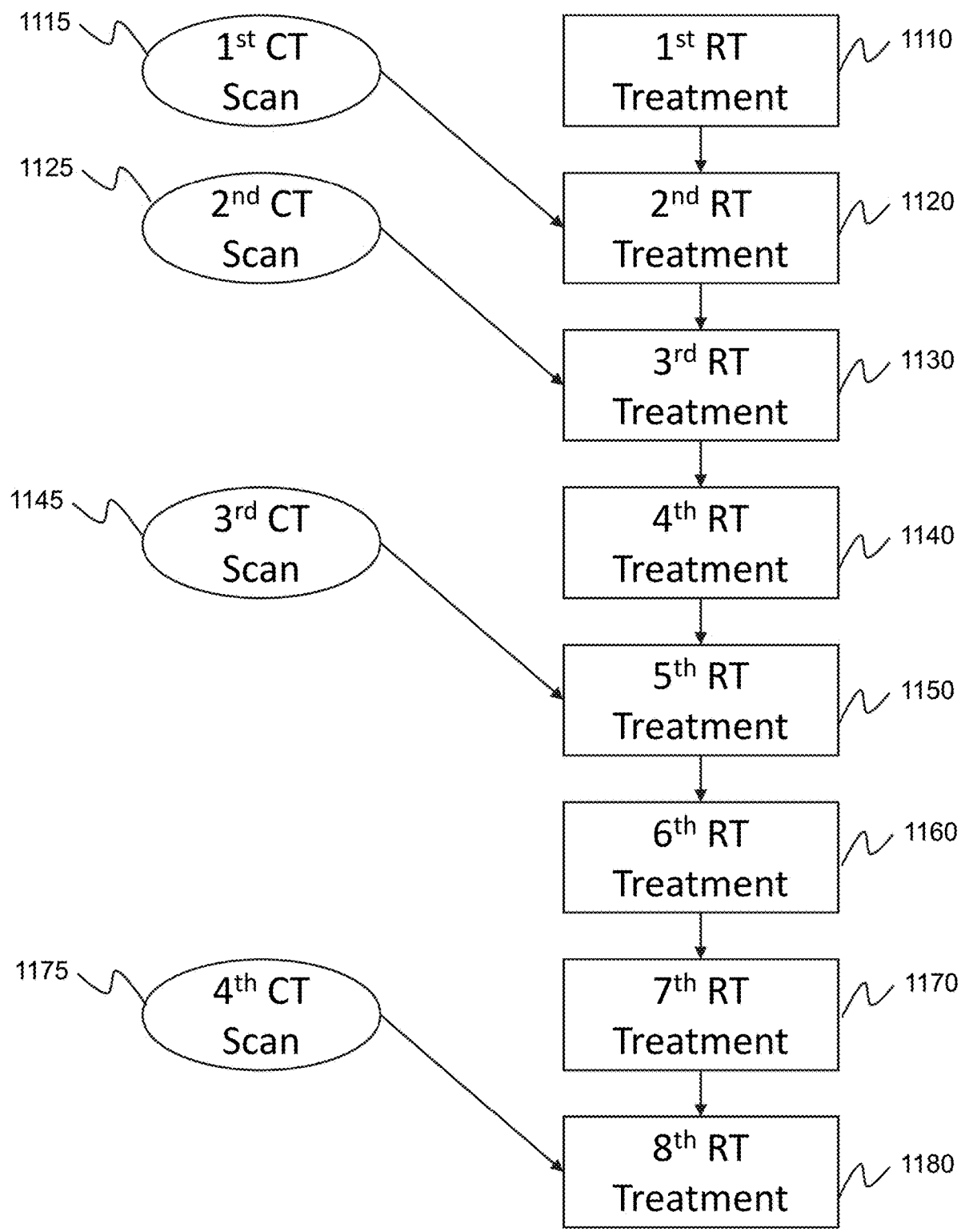
FIG. 11 is a schematic diagram illustrating an exemplary process of CT scans and RT treatments in different rotations according to some embodiments of the present disclosure.

FIG. 11 is a schematic diagram illustrating an exemplary process of CT scans and RT treatments in different rotations according to some embodiments of the present disclosure. In some embodiments, CT scans and/or RT treatment in each row of FIG. 11 may correspond to a rotation (or a rotation of 360 degrees) of a rotary ring (e.g., the rotary ring 114, the rotary ring 440, the rotary ring 630, the rotary ring 740). For example, the $2^{nd}$ CT scan 1125 and the $2^{nd}$ RT treatment 1120 may correspond to a second rotation. The CT scan may be performed by an imaging assembly (e.g., the second radiation source 111 and the radiation detector 112, the imaging radiation source 410 and the radiation detector 420, the imaging radiation source 710 and the radiation detector 720). The RT treatment may be performed by a treatment radiation source (e.g., the first radiation source 113, the treatment radiation source 430, the treatment radiation source 730). As shown in FIG. 11, an RT treatment in a present rotation may be related to a CT scan result and an RT treatment in a preceding rotation. For example, the $5^{th}$ RT treatment 1150 may be related to a $3^{rd}$ CT scan 1145 and a $4^{th}$ RT treatment 1140. More particularly, each rotation of the rotary ring may be associated with a treatment plan. The treatment plan may include a plurality of parameters associated with one or more radiation segments. The radiation segment may be an arc-shaped segment on the rotation trajectory of the rotary ring at which the treatment radiation source delivers the treatment beam to the treatment region. The parameters associated with the one or more radiation segments may include a desired segment shape, a desired segment intensity (e.g., a desired segment MU value, a desired segment MU rate), a desired segment angle range, and/or a desired relative position of the object relative to the rotary ring.

In some embodiments, the treatment plan or parameters thereof in a preceding rotation may be adjusted based on a CT scan result (e.g., CT image data) in the preceding rotation. The RT treatment in a present rotation may be determined by the adjusted treatment plan. In some embodiments, the processing module 1030 may cause the rotary ring to rotate a first full rotation and a second full rotation, the second full rotation being after the first full rotation. The processing module 1030 may then adjust, based on radiation detected by the radiation detector in the first full rotation, parameters associated with the radiation segments at which the first radiation source emits a first cone beam in the second full rotation. Further, the processing module 1030 may control an emission of the first cone beam based on the adjusted parameters associated with the radiation segments.

Similarly, the processing module 1030 may adjust, based on radiation detected by the radiation detector in the second full rotation, parameters associated with radiation segments at which the first radiation source emits a first cone beam in the third full rotation and control an emission of the first cone beam based on the adjusted parameters. The similar processes of adjusting parameters associated with the radiation segments and controlling the emission of the first cone beam based on adjusted parameters may be performed repeatedly in subsequent rotations.

In some embodiments, the processing module 1030 may adjust, based on radiation detected by the radiation detector in a present rotation, parameters associated with the radiation segments that follow the radiation detection by the radiation detector in the present rotation. The processing module 1030 may control the RT treatment (or the emission of the first cone beam) at the radiation segments that follow the radiation detection by the radiation detector based on the adjusted parameters associated with the radiation segments in the present rotation.

Figure 12:
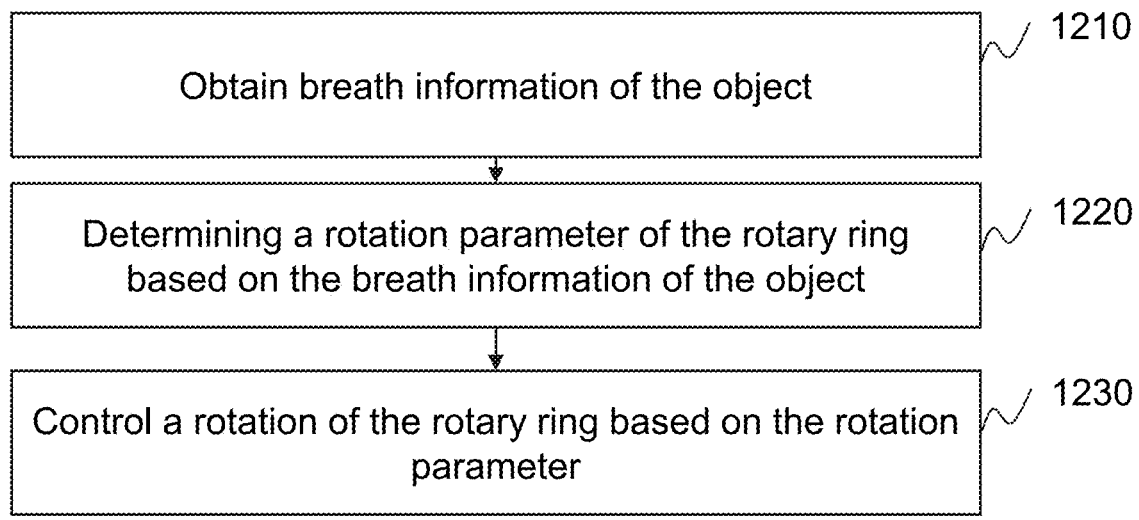
FIG. 12 is a flowchart illustrating an exemplary process for controlling a rotation of the rotary ring based on respiration information of an object.

FIG. 12 is a flowchart illustrating an exemplary process for controlling a rotation of the rotary ring based on respiration information of an object. In some embodiments, one or more operations of process 1200 may be implemented in the radiation system 100 illustrated in FIG. 1. For example, the process 1200 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 10, or the like). As another example, at least a portion of the process 1200 may be implemented on the radiation delivery device 110. The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1210, the processing module 1030 may obtain respiration information of the object. The respiration information of the object may include an average respiration period, a minimum respiration period, a maximum respiration period of the object. In some embodiments, the respiration period may be defined as a period that the object inhales and exhales. The respiration information of the object may also include the average inhale period and average exhale period.

In some embodiments, the respiration information may be obtained by a respiration information acquisition device. For example, the respiration information acquisition device may be a camera. The camera may be configured to monitor the mouth of the object and determine the respiration information based on the shape and size of the mouth. As another example, the respiration information acquisition device may include a gas detector (e.g., an air mask). The gas detector may be placed on the mouth and/or nose of a patient and act as an air exchanging channel. The respiration information may be determined based on the air flowing in/out of the air exchange channel.

In 1220, the processing module 1030 may determine a rotation parameter of the rotary ring based on the respiration information of the user. Merely by way of example, the respiratory motion of the lungs and/or the diaphragm, and its effect on other organs may influence the quality of CT scan or the radiotherapy treatment disclosed elsewhere in the present application. The rotation speed (i.e., a rotation parameter) of the rotary ring may be controlled to reduce the influence of the respiratory motion. In some embodiments, the rotation speed (or the rotation parameter) of the rotary ring may be controlled to be not more than half of the average respiration period. For example, the rotation speed (or the rotation parameter) of the rotary ring may be controlled to 1 rotation per second if the average respiration period is 3 seconds. In some embodiments, the period that the rotary ring rotates a full rotation may be less than 30 seconds. In some embodiments, the period that the rotary ring rotates a full rotation may be a fixed value, e.g., 1 second, 2 seconds, 5 seconds, 10 seconds, 30 seconds, etc. As another example, the rotation speed of the rotary ring may be changed dynamically based on the average respiration period or other respiration information.

In 1230, the processing module 1030 may control a rotation of the rotary ring based on the rotation parameter. For example, the processing module 1030 may send an instruction to the motor of the rotary ring to increase or decrease the rotation speed of the rotary ring.

Figure 13:
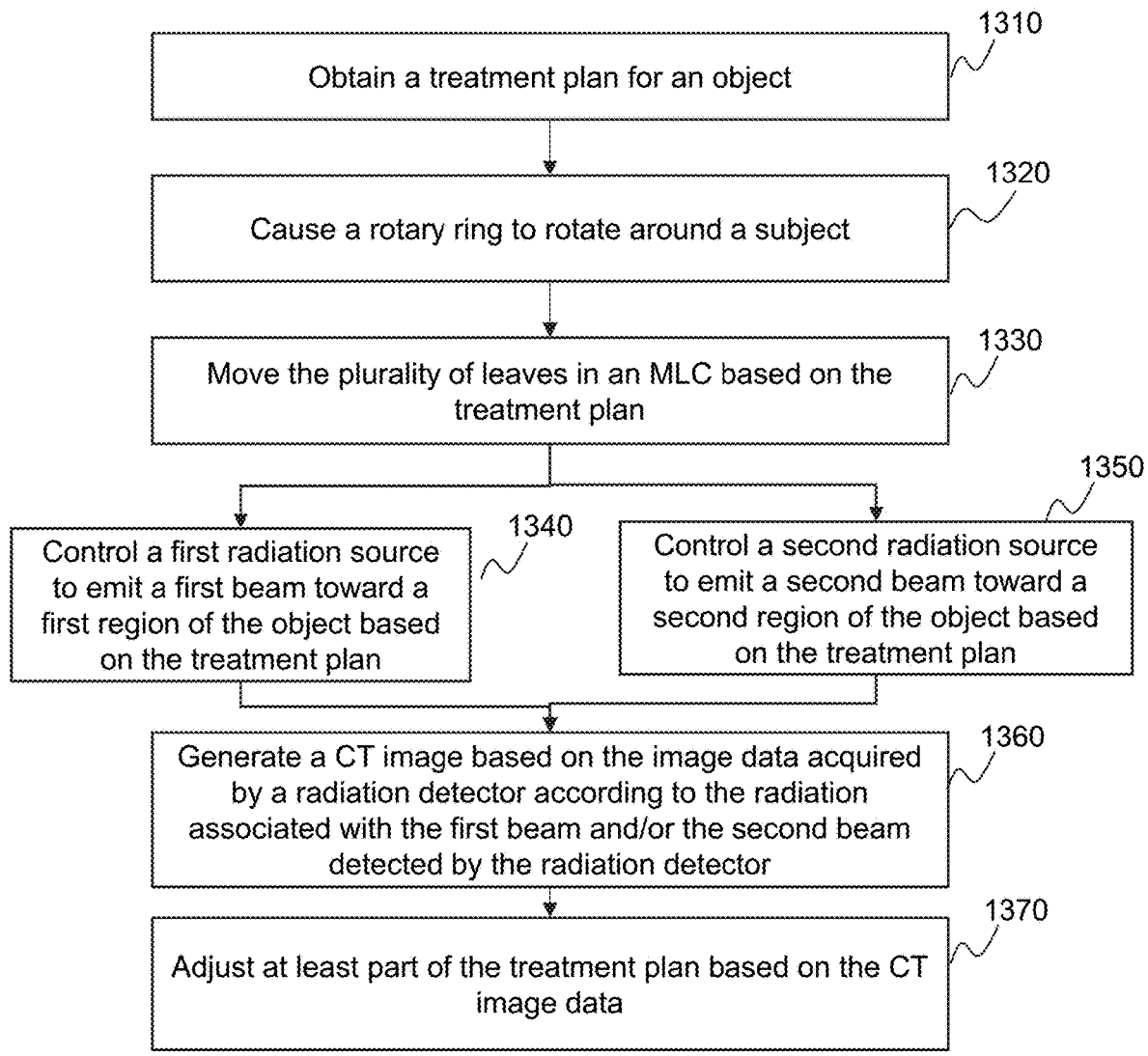
FIG. 13 is a flowchart illustrating an exemplary process for controlling emissions of beams from a first radiation source and a second radiation source.

FIG. 13 is a flowchart illustrating an exemplary process for controlling emissions of beams from a first radiation source and a second radiation source. In some embodiments, one or more operations of process 1300 may be implemented in the radiation system 100 illustrated in FIG. 1. For example, the process 1300 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 10, or the like). As another example, at least a portion of the process 1300 may be implemented on the radiation delivery device 110. The operations of the illustrated process presented below are intended to be illustrative. In some embodiments, the process 1300 may be accomplished with one or more additional operations not described, and/or without one or more of the operations discussed. Additionally, the order in which the operations of the process 1300 as illustrated in FIG. 13 and described below is not intended to be limiting.

In 1310, the acquisition module 1010 may obtain a treatment plan for an object. The treatment plan may include parameters for controlling the delivered radiation to be delivered to a treatment region (e.g., a tumor region) and sparing the surrounding healthy tissue surrounding the treatment region from the radiation damage. The treatment plan may be determined based on a set of one or more optimization goals and/or one or more constraints of a radiation delivery device (e.g., the radiation delivery device 110). The treatment plan may include parameters associated with at least one radiation segment. The radiation segment may be an arc-shaped segment on the rotation trajectory of the rotary ring at which a treatment radiation source (e.g., the first radiation source 113, the treatment radiation source 430, the treatment radiation source 730) delivers the treatment beam to the treatment region. The parameters associated with the radiation segments may include a desired segment shape (e.g., a desired shape of the aperture formed by an MLC (e.g., the MLC 450, the MLC 750, the MLC 900)), a desired segment intensity (e.g., a desired segment MU value, a desired segment MU rate), a desired segment angle range, and/or a desired relative position of the object relative to the rotary ring. Details regarding the generation of the treatment plan may be found in PCT application No. PCT/CN2018/

085279, entitled "SYSTEMS AND METHODS FOR GENERATING RADIATION TREATMENT PLAN" filed on May 2, 2018, the disclosure of which is expressly incorporated herein to its entirety.

In some embodiments, the acquisition module 1010 may obtain the treatment plan from one or more components of the radiation system 100, such as a storage device (e.g., the storage device 150), a terminal (e.g., the terminal 130), or the like. Alternatively, or additionally, the acquisition module 1010 may obtain the treatment plan from an external source via the network 120. For example, the acquisition module 1010 may obtain the treatment plan from an electronic medical record, a medical database, etc.

In 1320, the control module 1020 may cause a rotary ring to rotate around the object. As described elsewhere in the present disclosure, a treatment radiation source (e.g., the first radiation source 113, the treatment radiation source 430, the treatment radiation source 730), an imaging radiation source (e.g., the second radiation source 111, the imaging radiation source 410, the imaging radiation source 710) and a radiation detector (e.g., the radiation detector 112, the radiation detector 420, the radiation detector 720) may be mounted on the rotary ring (e.g., the rotary ring 114, the rotary ring 440, the rotary ring 630, the rotary ring 740), and the rotary ring may rotate around the object. The angular offset between the treatment radiation source and the imaging radiation source in the plane of rotation of the rotary ring may remain unchanged during the rotation of the rotary ring.

It may be desirable to monitor a location or shape of the treatment region by imaging the treatment region (or the object), so that the radiotherapy may be guided based on the location of the treatment region. The radiotherapy (or a portion of the radiotherapy procedure) may be performed simultaneously with the imaging operation (e.g., a 3-D imaging) during the rotation of the rotary ring. In some embodiments, the 3-D imaging may include generating a 3-D image based on a received radiation associated with either of or both the first cone beam and the second beam. Merely by way of example, the first cone beam and the second beam may be emitted in a same full rotation or a same fraction of a full rotation. In some embodiments, the change of location or shape (e.g., the respiratory motion, the cardiac motion) of the treatment region of the object may be determined so that the control module 1020 may control the rotary ring as well as the treatment radiation source and the imaging assembly (including the imaging radiation source and the radiation detector) to rotate at a relatively high speed to ensure that image(s) generated by the imaging assembly have relatively high quality (e.g., relatively high clarity, relatively low level of artifact).

In 1330, the control module 1020 may move the plurality of leaves in an MLC based on the treatment plan. The MLC (e.g., the MLC 450, the MLC 750, the MLC 900) may modify the shape of the beam emitted from the first radiation source 113. The treatment plan may include a desired segment shape of a radiation segment. The desired segment shape may correspond to a shape of desired treatment region (e.g., the treatment region 940). The leaves of the MLC may be moved based on the treatment plan such that an aperture formed by the leaves may modify the shape of the beam emitted from the radiation source. The modified beam may be delivered toward and match (or approximately match) the desired treatment region.

In 1340, the control module 1020 may control a first radiation source to emit a first beam toward a first region of the object based on the treatment plan. The first radiation source may emit the first beam toward the treatment region of the object when the rotary ring (or the first radiation source) is rotating. In some embodiments, the first radiation source is a treatment radiation source, and the first region is a treatment region (e.g., a tumor). Alternatively, the first radiation source is an imaging radiation source, and the first region is an imaging region.

In some embodiments, the first radiation source may emit a plurality of first beams to the first region of the object at a plurality of radiation segments. The beam shapes and beam intensities in different radiation segments may be different. In some embodiments, the leaves of the MLC may be adjusted to provide beam shapes corresponding to the plurality of radiation segments. In some embodiments, the MLC may be adjusted during an interval between two radiation segments.

Merely by way of example, there are two radiation segments, such as a first segment and a second segment. Before the emission of the radiation beams, the first radiation source may be rotated to a first radiation position. The first radiation position may correspond to the radiation segment angle of a first radiation segment. The MLC may be adjusted to a first configuration that forms an aperture corresponding to the shape of the first radiation segment. Then the control module 1020 may control the first radiation source to emit a beam with a first beam intensity during the rotation in the first radiation segment. When the first radiation source is about to be out of the radiation angle of the first radiation segment, the control module 1020 may control the first radiation source to stop the emission of the beam. The control module 1020 may adjust the MLC to a second configuration that forms an aperture corresponding to the shape of a second radiation segment. When the first radiation source 113 rotates to the second radiation segment, the MLC may move its leaves to the second configuration, and the control module 1020 may control the first radiation source 113 to emit a beam with a second beam intensity during the rotation in the second radiation segment.

In 1350, the control module 1020 may control a second radiation source to emit a second beam toward a second region of the object based on the treatment plan. In some embodiments, the second radiation source may emit the second beam toward the second region of the object when the rotary ring (or the second radiation source) is rotating at a relatively high speed.

In some embodiments, the first radiation source and the second radiation source may perform the same functions. For example, the first radiation source and the second radiation source may both be configured to deliver treatment beams to the treatment region, or both configured to generate image data of the object (including the treatment region). In some embodiments, the first radiation source may be configured to deliver radiation to the treatment region, while the second radiation source may be configured to generate image data of the object (including the treatment region).

In 1360, the processing module 1030 may generate a CT image based on the image data acquired by a radiation detector (e.g., the radiation detector 112) according to the radiation associated with the first beam and/or the second beam being detected by the radiation detector. The first beam and/or the second beam may be emitted in a same full rotation or in a same fraction of a full rotation. The CT image may include a two-dimensional (2-D) image, a three-dimensional (3-D) image, or the like. In some embodiments, the image may include information related to one or more imaging regions of the object (e.g., a tumor, OAR, other healthy organs or tissue).

In some embodiments, the imaging assembly may scan the object to acquire image data continuously or discontinuously. The image data may be used to reconstruct or generate one or more images of the object. In some embodiments, the imaging assembly may scan the object at a certain interval (e.g., once every 5 degrees of a rotation, once every 10 degrees of a rotation, etc.). In some embodiments, to generate the image(s) in multiple layers, a bed supporting the object (e.g., the bed 115, the bed 460) may be moved, for example, along the Z-axis direction illustrated in FIG. 1. In some embodiments, when the bed is moved, the control module 1020 may cause the treatment radiation source to stop or pause the emission of the radiation beams. In some embodiments, the treatment plan may take the movement of the bed into consideration, and the treatment radiation source may keep emitting the radiation beams when the bed is moved.

In some embodiments, the processing module 1030 may reconstruct one or more the image(s) based on the image data acquired by the imaging assembly according to a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or a combination thereof.

In 1370, the control module 1020 (and/or the processing module 1030) may adjust at least part of the treatment plan based on the CT image data. In some embodiments, the processing module 1030 may compare the generated CT image data with treatment planning image data. The treatment planning image data may refer to image data that are used to generate or adjust the treatment plan. The processing module 1030 may determine whether the treatment plan needs to be adjusted based on a result of the comparison. In response to a result of the determination that the treatment plan needs to be adjusted, the control module 1020 may adjust at least part of the treatment plan, for example, at least one parameters associated with the treatment plan. More descriptions regarding the adjustment of the treatment plan may be found elsewhere in the present disclosure (e.g., FIG. 14 and the relevant descriptions thereof). In some embodiments, the control module 1020 may adjust the position of the object based on a result of the comparison but not adjust the treatment plan. Alternatively, the control module 1020 may adjust both the treatment plan and the position of the object.

Figure 14:
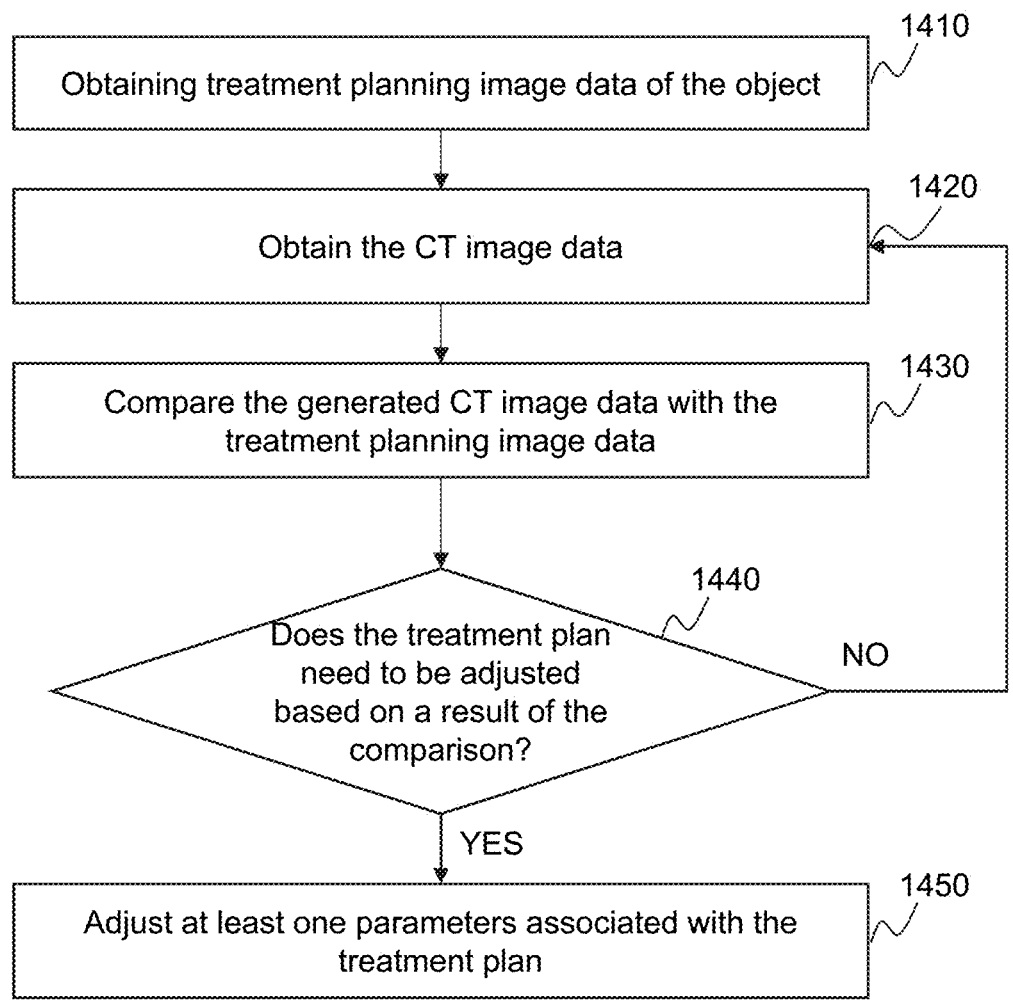
FIG. 14 is a flowchart illustrating an exemplary process for adjusting the treatment plan based on radiation detected by a radiation detector.

FIG. 14 is a flowchart illustrating an exemplary process for adjusting the treatment plan based on the detected radiation associated with the first radiation source and/or the second radiation source. In some embodiments, one or more operations of process 1400 may be implemented in the radiation system 100 illustrated in FIG. 1. For example, the process 1400 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 10, or the like). As another example, at least a portion of the process 1400 may be implemented on the radiation delivery device 110. The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting.

In 1410, the processing module 1030 may obtain treatment planning image data of the object. The treatment planning image data may refer to image data used to determine and/or adjust the treatment plan. In some embodiments, the treatment planning image data may be initial CT image data associated with the object. For example, the initial CT image data may be obtained by the second radiation source 111 and the radiation detector 112. As another example, the initial CT image data may be obtained by an imaging assembly outside the radiation delivery device 110.

In 1420, the processing module 1030 may obtain the CT image data of the object. The CT image data of the object may be generated by the operation 1360 in process 1300.

In 1430, the processing module 1030 may compare the generated CT image data with the treatment planning image data. In some embodiments, the processing module 1030 may determine whether a change of the location (and/or a change of shape) of treatment region related to the object has occurred and/or the magnitude of such change (if any) based on the comparison between the generated CT image data and the treatment planning image data. In some embodiments, the change of the location related to the object may refer to a change of the location of the treatment region (e.g., the tumor) and/or OAR, which may be caused by a movement of the object, for example, cardiac motions, respiratory motions of the lungs and/or the diaphragm, muscle contraction and relaxation, a displacement of the object relative to the table 115, or the like, or a combination thereof. By comparing the generated CT image data with the treatment planning image data, the processing module 1030 may determine the change of the location of the treatment region (e.g., the tumor) and/or OAR. In some embodiments, both the generated CT image data and the treatment planning image data may be 3-dimensional (3-D) image data. Alternatively, either or both of the generated CT image data and the treatment planning image data may be 2-dimensional (2-D) image data. In a case that one of the generated CT image data and the treatment planning image is 2-D and the other one is 3-D (e.g., the generated CT image data is 2-D and the treatment planning image data is 3-D), the treatment planning image data may be front projected to generate 2-D treatment planning image data and compared with the generated CT image data which is already in 2-D.

In 1440, the processing module 1030 may determine whether the treatment plan needs to be adjusted based on a result of the comparison. For example, the processing module 1030 may determine whether the change (or the magnitude thereof) of the location of the treatment region exceeds a threshold. The threshold may be predetermined according to different organs and objects. In response to a result of the determination that the change of the location of the treatment region does not exceed a threshold, the processing module 1030 may determine that the treatment plan does not need to be adjusted, the radiotherapy procedure may continue, and the process 1400 may proceed back to 1420 to obtain new CT image data. The new CT image data may undergo the similar operations 1430-1440. In response to a result of the determination that the change of the location of the treatment region exceeds a threshold, the processing module 1030 may determine that the treatment plan needs to be adjusted, and the process 1400 may proceed to 1450.

In 1450, the control module 1020 may pause or stop the emission of the plurality of radiation beams from the first radiation source. In some embodiments, when the emission of the radiation beam(s) from the first radiation source is paused or stopped, the control module 1020 may cause the first radiation source to stop rotating or rotate at a lower rotation speed. The processing module 1030 may adjust at least some of the parameters associated with the treatment plan based on the CT image data obtained in 1420 (and/or the comparison between the CT image data and the treatment planning image data). In some embodiments, some of the parameters associated with the radiation segments may be adjusted while others may remain the same. For example, if a change of shape of the treatment region is identified while the location of the treatment region and the center thereof remain unchanged, only the segment shapes of the radiation segments in the treatment plan may be adjusted while other parameters may not be adjusted.

After the adjustment to the treatment plan, the radiation delivery device may be controlled to work again, at a normal or reduced rotation speed and/or radiation intensity. In some embodiments, the adjusted treatment plan may replace the previous treatment plan and may be used in the rotations after the adjustment. Alternatively, the adjusted treatment plan is only used in a number of rotations, and the original treatment plan for the rotations after is then used.

FIG. 15 is a flowchart illustrating an exemplary process for adjusting one or more components of the radiation system based on the adjusted treatment plan. In some embodiments, one or more operations of process 1500 may be implemented in the radiation system 100 illustrated in FIG. 1. For example, the process 1500 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 10, or the like). As another example, at least a portion of the process 1500 may be implemented on the radiation delivery device 110. The operations of the illustrated process presented below are intended to be illustrative. In some embodiments, the process 1500 may be accomplished with one or more additional operations not described, and/or without one or more of the operations discussed. Additionally, the order in which the operations of the process 1500 as illustrated in FIG. 15 and described below is not intended to be limiting.

In 1510, the processing module 1030 may obtain an adjusted treatment plan. The adjusted treatment plan may be generated from operation 1450 of process 1400 described above. The adjusted treatment plan may include parameters associated with one or more radiation segments, which includes a desired (or an adjusted) segment shape, a desired (or an adjusted) segment intensity (e.g., a desired segment MU value, a desired segment MU rate), a desired (or an adjusted) segment angle range, and/or a desired (or an adjusted) relative position of the object relative to the rotary ring.

In 1520, the processing module 1030 may move the MLC according to the desired segment shape when a desired (or an adjusted) segment angle range is reached during the rotation of the rotary ring. For example, the processing module 1030 may determine a desired (or an adjusted) movement of each of the leaves in the MLC based on the desired (or an adjusted) segment shape and the current shape of the aperture. The processing module 1030 may send an instruction including the desired (or an adjusted) movement of each of the leaves in the MLC to a corresponding motor (e.g., motors 830) to move the leave such that the aperture formed by the moved leaves in the MLC satisfy the desired (or an adjusted) segment shape.

In 1530, the processing module 1030 may control the emission of the first beam and/or the second beam from the first radiation source and/or the second radiation source based on the desired (or an adjusted) segment intensity (e.g., a desired segment MU value, a desired segment MU rate). For example, the processing module 1030 may control the voltage or current supply of the first radiation source and/or the second radiation source to control the emission of the first beam and/or the second beam.

In 1540, the processing module 1030 may move the bed based on the desired (or an adjusted) relative position of the object relative to the rotary ring. For example, the processing module 1030 may determine a desired (or an adjusted) movement of the bed in the X,Y, or the Z-direction based on the desired (or an adjusted) relative position of the object with respect to the rotary ring and the current relative position of the object with respect to the rotary ring and send an instruction including the desired (or an adjusted) movement in the X, Y, or the Z-direction to a motor of the bed.

In some embodiments, the radiation detector (e.g., radiation detector 112, radiation detector 420, radiation detector 720) is disposed so as to receive substantially radiation originating from the second radiation source (e.g., second radiation source 111, imaging radiation source 410, imaging radiation 710) is a CT detector. CT detectors are normally designed to be used with helical scanning systems in which an imaging radiation source moves relative to an imaged object along the long axis of the object. In most cases, the imaged object is a patient, and the long axis is the head-foot axis. In most cases, the bed is moved along the long axis to produce the relative motion. The reason a helical scan is used is that most CT detectors have limited axial extent. In order to achieve a sufficient axial field-of-view, relative motion is usually necessary. When performing imaging during the treatment fraction, in many cases it is necessary to move the bed (e.g., in a first direction) to achieve sufficient axial field-of-view. However, this motion will also displace the treatment field with respect to the expected position. Thus, a treatment plan associated with the radiation system 100 may be adjusted to account for the motion of the treatment field. The adjustment of the treatment plan may be found in 1370 in FIG. 13 and/or 1450 in FIG. 14. If the treatment plan is not adjusted to account for this motion, since collimator elements such as jaws and MLC leaves may, in many cases, be too slow to efficiently account for bed motion, the processing module 1030 may dispose the first radiation source to move in a direction along the moving direction of the bed, so that the need to account for bed motion by collimator motion is reduced or obviated. The first radiation source may move at a speed equal to the speed of the bed. Alternatively, the 2-D MLC may be disposed to move in a direction along the moving direction of the bed. The 2-D MLC may move at a speed equal to the moving speed of the bed. Almost all 2-D MLCs include a carriage that can simultaneously move a bank of leaves along the direction of leaf travel. To achieve the desired relative motion when the direction of leaf travel is oriented along the plane of rotation, a carriage may be needed to move the leaves along the axial direction (direction of the bed).

In some embodiments, images generated by the second radiation source may be used to modify the position of the object with respect to the first radiation source such that a target tissue (e.g., a tumor) in the first region is centered at the isocenter of the radiation system 100. The isocenter of the radiation system 100 may be a rotational isocenter, which refers to the central point of the bore (e.g., the bore 117, the bore 480) or the point that is continuously passed by the first radiation beam emitted from the first radiation source when the rotary ring (e.g., the rotary ring 114, the rotary ring 440, the rotary ring 630, the rotary ring 740) is rotating. Alternatively, the respiration information obtained in 1210 in FIG. 12) may be used to modify the position of the object with respect to the first radiation source such that a target tissue in the first region is substantially centered at the rotational isocenter of the radiation system 100.

In many radiation therapy cases, the target tissue of the first region may be partitioned into one or more subvolumes that may be treated serially from many angles of beam incidence (during different rotation angles of the rotary ring). The processing module 1030 may be further configured to adjust a position of at least one of the subvolumes such that a center of the at least one of the subvolumes substantially overlaps with the isocenter of the radiation system 100. For example, a tumor that is substantially spherical, or contains a substantially spherical core subvolume may present as a target that requires little collimator adjustment as a function of beam incidence angle, providing the subvolume is centered at the rotational isocenter of the treatment system. In some embodiments, an imaging feedback provided by the radiation system 100 described here may be used to adjust the position of the tumor (or target volume/subvolume) relative to the treatment source in such a way as to position this volume (or subvolume) of the tumor at the rotational isocenter, in order to reduce the collimator motion required. Such an arrangement can increase treatment efficiency especially in cases where collimator speed (usually MLC leaf speed, in the case of 2-D MLCs, which are MLCs that shape a cone beam into a 2-D radiation field) is the limiting factor in treatment delivery speed. MLC speed is likely the limiting factor in contemporary therapy systems capable of fast gantry rotation (>2 rotations/minute) and high radiation output rates (>300 MU/min).

In most implementations of arc therapy systems, slow rotation speeds (<2 rotations/min) are employed, and treatments are delivered using 1 or 2 rotations. In order to obtain frequently updated images of tissues during treatment, larger rotation rates are favored. In some embodiments, the advantage of decomposing the treatment into subvolumes, such as those described above, and serially addressing such subvolumes as described above, may include preventing collimator speed limitations from reducing beam-on duty cycle and overall treatment efficiency.

We have described embodiments of systems for simultaneous imaging and radiation therapy. In the context of a pulsed, and variable-duty-cycle radiation delivery and imaging system (e.g., the radiation system 100), the term "simultaneous" requires disambiguation. Linear accelerator sources (e.g., the first radiation source 113 and the second radiation source 111) typically produce pulses with duty cycles (e.g., a ratio between a on-period and a off-period) of the order of 1:1000. For the vast majority of time during a treatment session when the beam is considered "on", no radiation is being produced. It is possible to image during the off-period. Such imaging is still regarded as occurring simultaneously with the treatment. This is because the treatment has already commenced, and will continue within a time period that is very short. There may be periods of the order 1-10,000 ms, between parts of the treatment delivery, where the treatment source is switched off or collimated off. Imaging that occurs during this time, as well as imaging that occurs while the treatment beam is on, are both regarded as imaging that is simultaneous with treatment. In contrast, imaging that occurs after the treatment beam has been off (i.e., is not imparting substantial dose to the patient) for more than a complete system rotation, and imaging that occurs more than 10 s after the treatment beam has been turned off, is not regarded, for the purposes of the teachings contained herein, as imaging that is simultaneous with the treatment.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object-oriented programming language such as Java, Scala, Smalltalk, Eiffel, JADE, Emerald, C++, C #, VB.

NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped in a single embodiment, figure, or descriptions thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation system, comprising:
   a bore configured to accommodate an object;
   a rotary ring;
   a first radiation source mounted on the rotary ring and configured to emit a first cone beam toward a first region of the object, with a 2-D collimator positioned between a center of the bore and the first radiation source to form at least one aperture, the at least one aperture being configured to modify a shape of the first cone beam;
   a second radiation source mounted on the rotary ring and configured to emit a second beam toward a second region of the object, the second region including at least a part of the first region; and
   a processor configured to cause the radiation system to:
      obtain a treatment plan of the object, the treatment plan including parameters associated with one or more radiation segments;
      cause the rotary ring to rotate around the object in one direction continuously for at least two full rotations, wherein a period that the rotary rind rotates a full rotation is less than 30 seconds;
      adjust the at least one aperture of the 2-D collimator based on the parameters associated with the one or more radiation segments; and
      control an emission of at least one of the first cone beam or the second beam based on the parameters associated with the one or more radiation segments to perform a treatment and a 3-D imaging simultaneously.

2. The radiation system of claim 1, wherein the 2-D collimator comprises a multi-leaf collimator (MLC) including a plurality of leaves to form the aperture.

3. The radiation system of claim 1, wherein when the rotary ring rotates, an angular offset between the first radiation source and the second radiation source in a plane of the rotation of the rotary ring remains unchanged.

4. The radiation system of claim 1, wherein the parameters associated with the one or more radiation segments include at least one of a desired segment shape, a desired segment MU value, a desired segment MU rate, a desired segment angle range, or a desired relative position of the object relative to the rotary ring.

5. The radiation system of claim 1, further comprising:
   a radiation detector configured to detect radiation impinging on the radiation detector, wherein the processor is further configured to cause the radiation system to:

obtain treatment planning image data of the object associated with the treatment plan;
generate a radiograph or CT image data based on the detected radiation by the radiation detector, the detected radiation being associated with at least one of the first cone beam or the second beam;
compare the generated radiograph or CT image data with the treatment planning image data;
determine whether the treatment plan needs to be adjusted based on a result of the comparison between the generated radiograph or CT image data and the treatment planning image data; and
adjust, based on a result of the determination that the treatment plan needs to be adjusted, at least one of the parameters associated with the one or more radiation segments.

6. The radiation system according to claim 5, wherein the radiograph or the CT image data is obtained during a part of a rotation of the rotary ring.

7. The radiation system of claim 1, further comprising:
a bed configured to support the object, wherein the processor is further configured to cause the radiation system to adjust a position of the bed based on a desired position of the object with respect to the rotary ring.

8. The radiation system of claim 1, wherein the processor is further configured to cause the radiation system to:
obtain respiration information of the object;
determine a rotation parameter of the rotary ring based on the respiration information of the object; and
control a rotation of the rotary ring based, at least in part, on the determined rotation parameter.

9. The radiation system of claim 8, wherein the rotation parameter includes a rotation speed.

10. The radiation system of claim 1, further comprising:
a radiation detector configured to detect radiation impinging upon the detector, and wherein the processor is further configured to cause the radiation system to:
cause the rotary ring to rotate a first full rotation and a second full rotation, the second full rotation being after the first full rotation;
adjust, based on radiation detected by the radiation detector in the first full rotation, parameters associated with the radiation segments at which the first radiation source emits a first cone beam in the second full rotation; and
control an emission of the first cone beam based on the adjusted parameters associated with the radiation segments.

11. The radiation system of claim 1, further comprising:
a radiation detector configured to detect radiation impinging upon the detector, wherein the processor is further configured to cause the radiation system to:
cause the rotary ring to rotate;
adjust, based on radiation detected by the radiation detector in the present rotation, parameters associated with radiation segments that follow the radiation detection by the radiation detector in the present rotation; and
control an emission of the first cone beam at the radiation segments that follow the radiation detection by the radiation detector based on the adjusted parameters associated with the radiation segments that follow the radiation detection by the radiation detector in the present rotation.

12. The radiation system of claim 1, wherein a cone angle of the second beam is greater than a cone angle of the first cone beam.

13. The radiation system of claim 1, further comprising:
a CT detector configured to detect radiation emitted by the second radiation source after attenuation by the object.

14. The radiation system of claim 1, further comprising:
a flat panel detector configured to detect radiation emitted by the first radiation source after attenuation by the object.

15. The radiation system of claim 10, further comprising:
a bed configured to support the object and move in a first direction and cause a displacement between the first radiation source and the object in the first direction during the first full rotation, wherein the processor is further configured to cause the radiation system to move the first radiation source in the first direction to reduce or eliminate the displacement before or during the second full rotation.

16. The radiation system of claim 15, wherein the first radiation source moves at a speed equal to a speed of the bed.

17. The radiation system of claim 10, further comprising:
a bed configured to support the object and move in a first direction and cause a displacement between the first radiation source and the object in the first direction during the first full rotation, wherein the processor is further configured to cause the radiation system to dispose the 2-D collimator of the first radiation source to move in the first direction to reduce or eliminate the displacement before or during the second full rotation.

18. The radiation system of claim 17, wherein the 2-D collimator of the first radiation source moves at a speed equal to a moving speed of the bed.

19. The radiation system of claim 1, wherein to perform the 3-D imaging, the processor is configured to cause the system to_perform at least one of:
generating a 3-D image based on received radiation associated with the first cone beam and the second beam,
generating a 3-D image based on received radiation associated with the first cone beam and the second beam emitted in a same full rotation, or
generating a 3-D image based on received radiation associated with the first cone beam and the second beam emitted in a same fraction of a full rotation.

20. The radiation system of claim 1, wherein electric power is transferred to the first radiation source and the second radiation source via a slip ring.

21. The radiation system of claim 1, further comprising:
a detector paired with the second radiation source, configured to detect radiation associated with the second beam, wherein control and imaging data are transferred to and from the paired second radiation source and detector via a slip ring.

22. A radiation system, comprising:
a bore configured to accommodate an object;
a rotary ring;
a first radiation source mounted on the rotary ring and configured to emit a first cone beam toward a first region of the object, with a 2-D collimator positioned between a center of the bore and the first radiation source to form at least one aperture, the at least one aperture being configured to modify a shape of the first cone beam;
a second radiation source mounted on the rotary ring and configured to emit a second beam toward a second region of the object, the second region including at least a part of the first region; and
a processor configured to cause the radiation system to:

obtain a treatment plan of the object, the treatment plan including parameters associated with one or more radiation segments;

cause the rotary rind to rotate around the object in one direction continuously for at least two full rotations, wherein a period that the rotary rind rotates a full rotation is less than 30 seconds;

adjust a position of the object relative to the first cone beam based on the parameters associated with the one or more radiation segments; and control an emission of at least one of the first cone beam or the second beam based on the parameters associated with the one or more radiation segments to perform a treatment and a 3-D imaging simultaneously.

23. The radiation system of claim 1, wherein the period that the rotary ring rotates a full rotation is changed dynamically based on an average respiration period of the object and controlled to be not more than half of the average respiration period of the object.

* * * * *